US008546438B2

(12) United States Patent
Thede et al.

(10) Patent No.: US 8,546,438 B2
(45) Date of Patent: Oct. 1, 2013

(54) SUBSTITUTED (THIOPHENYL-CARBONYL) IMIDAZOLIDINONES, AND USE THEREOF

(76) Inventors: Kai Thede, Berlin (DE); Susanne Greschat, Wagenfeld (DE); Steffen Wildum, Schwelm (DE); Daniela Paulsen, Wuppertal (DE)

( * ) Notice: Subject to any disclaimer, the term of this patent is extended or adjusted under 35 U.S.C. 154(b) by 0 days.

(21) Appl. No.: 13/162,522

(22) Filed: Jun. 16, 2011

(65) Prior Publication Data
US 2012/0022123 A1 Jan. 26, 2012

Related U.S. Application Data

(63) Continuation of application No. PCT/EP2009/008992, filed on Dec. 15, 2009.

(30) Foreign Application Priority Data

Dec. 17, 2008 (DE) .................. 10 2008 062 863

(51) Int. Cl.
A61K 31/4166 (2006.01)
C07D 233/32 (2006.01)

(52) U.S. Cl.
USPC ....................................... 514/386; 548/316.4

(58) Field of Classification Search
USPC ....................................... 548/316.4; 514/386
See application file for complete search history.

(56) References Cited

U.S. PATENT DOCUMENTS

| 3,806,506 | A | 4/1974 | Felauer et al. |
| 4,684,652 | A | 8/1987 | Dubroeucq et al. |
| 5,134,142 | A | 7/1992 | Matsuo et al. |
| 5,432,835 | A | 7/1995 | Hasimoto |
| 5,571,810 | A | 11/1996 | Matsuo et al. |
| 5,624,941 | A | 4/1997 | Barth et al. |
| 5,627,203 | A | 5/1997 | Rault et al. |
| 6,143,780 | A | 11/2000 | Brouwer et al. |
| 7,622,471 | B2 | 11/2009 | Kanaya et al. |
| 8,314,089 | B2 | 11/2012 | Schohe-Loop et al. |
| 8,324,268 | B2 | 12/2012 | Thede et al. |
| 8,399,682 | B2 | 3/2013 | Thede et al. |
| 2004/0116425 | A1 | 6/2004 | Li et al. |
| 2005/0054707 | A1 | 3/2005 | Edwards et al. |
| 2008/0064682 | A1 | 3/2008 | Kanaya et al. |

FOREIGN PATENT DOCUMENTS

| DE | 10 2004 054 666 | 5/2006 |
| EP | 0 065 295 | 11/1982 |
| EP | 0 112 776 | 7/1984 |
| EP | 0 418 845 | 3/1991 |
| EP | 0 554 829 | 8/1993 |
| EP | 0 576 357 | 12/1993 |
| EP | 1 591 443 | 11/2005 |
| EP | 1 743 637 | 1/2007 |
| EP | 1762 568 | 3/2007 |
| WO | WO-91/19708 | 12/1991 |
| WO | WO-94/27979 | 12/1994 |
| WO | WO-97/19940 | 6/1997 |
| WO | WO-02/00649 | 1/2002 |
| WO | WO-02/100853 | 12/2002 |
| WO | WO-03/014107 | 2/2003 |
| WO | WO-03/037274 | 5/2003 |
| WO | WO-2004/016592 | 2/2004 |
| WO | WO-2004/024147 | 3/2004 |
| WO | WO-2004/031178 | 4/2004 |
| WO | WO-2004/050632 | 6/2004 |
| WO | WO-2004/076453 | 9/2004 |
| WO | WO-2005/000820 | 1/2005 |
| WO | WO-2005/002576 | 1/2005 |
| WO | WO-2005/007625 | 1/2005 |
| WO | WO-2005/035488 | 4/2005 |
| WO | WO-2005/080343 | 9/2005 |
| WO | WO-2006/015860 | 2/2006 |
| WO | WO-2006/023462 | 3/2006 |
| WO | WO-2006/062982 | 6/2006 |
| WO | WO-2006/062984 | 6/2006 |
| WO | WO-2006/065209 | 6/2006 |
| WO | WO-2006/099231 | 9/2006 |
| WO | WO-2007/002559 | 1/2007 |
| WO | WO-2007/009701 | 1/2007 |
| WO | WO-2007/020388 | 2/2007 |
| WO | WO-2008/043775 | 4/2008 |
| WO | WO-2008/080056 | 7/2008 |
| WO | WO-2008/090382 | 7/2008 |
| WO | WO-2009/115213 | 9/2009 |
| WO | WO-2009/115252 | * 9/2009 |

OTHER PUBLICATIONS

Carpenter et al., J. Am. Med. Assoc. (200) 283:381-390.
Database PubChem, Accession No. ZINC04827711, Sep. 12, 2005.
Database PubChem, Accession No. CID3315199, Sep. 7, 2005.
Database PubChem, Accession No. ZINC04560769, Sep. 18, 2005.
Database PubChem, Accession No. ZINC04374875, Sep. 13 2005.
Database PubChem, Accession No. ZINC04908325, Sep. 14, 2005.
Database PubChem, Accession No. ZINC04407915, Sep. 18, 2005.
Finzi et al., Nature Med. (1999) 5:512-517.
Flexner, Nature Reviews Drug Discovery (2007) 6:959-966.
Genin et al., J. Med. Chem. (2000) 43:1034-1040.
International Search Report for PCT/EP2009/01877, mailed on Feb. 11, 2010, 6 pages.
International Preliminary Report on Patentability for PCT/EP2009/001877, issued on Oct. 5, 2010, 9 pages.
Kavlick and Mitsuya, Antiretroviral Chemotherapy (Hrsg. De Clercq E.) (2001) ASM Press, pp. 279-312.
Kort et al., J. Med. Chem. (2008) 51:407-416.
Medveczky et al., BMC Medicine (2004) 2:34 1-9.
Palella et al., New England Journal of Medicine (1998) 238:853-860.
Ramratnam et al., Nature Med. (200) 6:82-85.
Richman, Nature (2001) 410:995-1001.

(Continued)

Primary Examiner — Kamal A. Saeed
Assistant Examiner — Janet L Coppins
(74) Attorney, Agent, or Firm — Morrison & Foerster LLP

(57) ABSTRACT

The present invention relates to novel substituted (thiophenyl-carbonyl)imidazolidinones, methods for their production, their use for the treatment and/or prevention of diseases, as well as their use for the production of medicaments for the treatment and/or prophylaxis of diseases, especially retroviral diseases, in humans and/or animals.

12 Claims, No Drawings

(56) References Cited

OTHER PUBLICATIONS

Romero et al., Journal of Medicinal Chemistry (1994) 37:999-1014.
International Search Report for PCT/EP2009/001714, mailed on May 12, 2009, 2 pages.
International Preliminary Report on Patentability for PCT/EP2009/001714, issued on Oct. 5, 2010, 5 pages.
U.S. Appl. No. 12/884,113, filed Jul. 2011, Schohe-Loop et al.
O'Neill, "The Diversity of Retroviral Diseases of the Immune System," Immunology and Cell Biology (1992) 70:193-199.
Van Rompay, "Evaluation of Antiretrovirals in Animal Models of HIV Infection," Antiviral Research (2010) 85:159-175.
West et al., "Targeting HIV-1 Protease: A Test of Drug-Design Methodologies," TIPS (1995) 16:67-75.
Non-Final Office Action for U.S. Appl. No. 12/884,113, mailed Jan. 26, 2012.
Response to Non-Final Office Action for U.S. Appl. No. 12/884,113, mailed Apr. 18, 2012.
Non-Final Office Action for U.S. Appl. No. 12/885,340, mailed May 10, 2012.
Non-Final Office Action for U.S. Appl. No. 13/162,521, mailed Dec. 23, 2011.
Response to Non-Final Office Action for U.S. Appl. No. 13/162,521, mailed Mar. 22, 2012.
Supplemental Response to Non-Final Office Action to U.S. Appl. No. 13/162,521, mailed Mar. 29, 2012.
Notice of Allowance for U.S. Appl. No. 12/885,340, mailed Nov. 6, 2012.
Notice of Allowance for U.S. Appl. No. 12/884,113, mailed Jul. 12 2012.
Notice of Allowance for U.S. Appl. No. 13/162,521, mailed Aug. 3, 2012.
Response to Non-Final Office Action for U.S. Appl. No. 12/885,340, mailed Aug. 9, 2012.

\* cited by examiner

SUBSTITUTED (THIOPHENYL-CARBONYL) IMIDAZOLIDINONES, AND USE THEREOF

CROSS REFERENCES TO RELATED APPLICATIONS

This application is a continuation of international patent application PCT/EP2009/08992, filed on Dec. 15, 2009 designating the U.S., which international patent application has been published in German language and claims priority from German patent application DE 10 2008 062 863.8, filed on Dec. 17, 2008. The entire contents of these priority applications are incorporated herein by reference.

BACKGROUND OF THE INVENTION

The present invention relates to novel substituted (thiophenyl-carbonyl)imidazolidinones, methods for their preparation, their use for the treatment and/or prophylaxis of diseases, as well as their use for the manufacture of medicaments for the treatment and/or prophylaxis of diseases, especially of retroviral diseases, in humans and/or animals.

HIV (human immunodeficiency virus) causes a chronic persistent progressive infection. The disease proceeds via various stages from the asymptomatic infection to the pathological condition AIDS (acquired immunodeficiency syndrome). AIDS is the final stage of the disease caused by infection. The HIV/AIDS disease is characterized by a long clinical latency period with persistent viraemia which, in the final stage, leads to the failure of the immune defences.

The introduction of the anti-HIV combination therapy made it possible in the 1990s to effectively slow the down progression of the disease and thus to prolong substantially the life expectancy of HIV-infected patients (Palella, et al., *N. Engl. J. Med.* 1998, 238, 853-860).

The anti-HIV substances currently on the market inhibit the replication of the HI virus by inhibiting the essential viral enzymes reverse transcriptase (RT), protease or integrase, or the entry of HIV into the target cell (review in Flexner, *Nature Reviews Drug Discovery* 2007, 6, 959-966). There are two classes of RT inhibitors: nucleosidic and nucleotidic RT inhibitors (NRTI) act through competitive inhibition or chain termination in the DNA polymerization. Non-nucleosidic RT inhibitors (NNRTI) bind allosterically to a hydrophobic pocket in the vicinity of the active centre of the RT and bring about a conformational change in the enzyme. The currently available protease inhibitors (PI) block the active centre of the viral protease and thus prevent the maturation of newly produced particles into infectious virions. The only currently authorized integrase inhibitor Raltegravir binds in the active centre of the HIV integrase and prevents the integration of the proviral DNA into the host cell genome. Entry inhibitors (fusion inhibitors and coreceptor antagonists) prevent the HIV infection of cells by interacting with the HIV coat protein or by blocking the cellular coreceptors CCR5 or CXCR4.

Since monotherapy with the currently available anti-HIV medicaments leads in a very short time to a failure of the therapy owing to a selection of resistant viruses, usually a combination therapy with several anti-HIV substances from different classes takes place (highly active antiretroviral therapy=HAART; Carpenter, et al., *J. Am. Med. Assoc.* 2000, 283, 381-390).

Despite the advances in antiretroviral chemotherapy, recent investigations show that an eradication of HIV and, associated therewith, a cure of the HIV infection is not to be expected with the available medicaments. The latent virus remains in dormant lymphocytes and represents a reservoir for a reactivation and thus for a renewed spread of the virus (Finzi, et al., *Nature Med.* 1999, 5, 512-517; Ramratnam, et al., *Nature Med.* 2000, 6, 82-85). HIV-infected patients are therefore life-long dependent on an efficient antiviral therapy. Despite combination therapy, a selection of resistant viruses occurs after some time. Since resistance mutations characteristic for each therapeutic class accumulate, the failure of one therapy often means a loss of effect of the complete class of substances. This cross-resistance problem is most pronounced with the class of NNRTIs because in this case a single point mutation in the RT may often be sufficient to bring about a loss of effect of all NNRTIs (review in Kavlick & Mitsuya, *Antiretroviral Chemotherapy* (editor De Clercq E.), 2001, ASM Press, 279-312).

The development of resistances is usually favoured by the poor compliance of the patients which is caused by an unfavourable profile of side effects and a complicated dosage regimen for the anti-HIV medicaments.

There is thus a pressing need for novel therapeutic options for controlling an HIV infection. For this purpose, an urgent aim of HIV therapy research is to identify novel chemical lead structures which either address a novel target in the replication of HIV and/or are effective against the growing number of resistant clinical HIV isolates.

WO 91/19708 A1 discloses thiophenecarboxamides having pain-alleviating and anti-inflammatory effects. EP 0 065 295 A1 discloses thiophenecarboxamides for treating cardiovascular disorders. WO 94/27979 A1 discloses thiophenecarboxamides as modulators of peptides of the endothelin type. WO 02/00649 A1, WO 2006/062982 A2 and WO 2006/062984 A2 describe thiophenecarboxamides as inhibitors of various kinases. Certain thiophenecarboxamides as intermediates in the synthesis of polycyclic compounds are known from U.S. Pat. No. 5,627,203 and WO 03/014107 A1. Thiophenecarboxamides as inhibitors of protein prenylation are known from US 2004/0116425 A1 and WO 2004/016592 A1. WO 2005/035488 A2 describes thiophenecarboxamides as antagonists of the cannabinoid receptor $CB_1$, and WO 2006/023462 A1 describes thiophenecarboxamides as antagonists of the histamine H3 receptor. Thiophenecarboxamides for the treatment of diseases caused by prions, cancer and disorders of the central nervous system and also for regulating stem cells are known from WO 2008/0903820 A1.

SUMMARY OF THE INVENTION

Against this background, it is an object of the present invention is to provide novel compounds having equal or improved antiviral activity for treating viral infectious diseases in humans and animals, which compounds do not have the disadvantages described above.

Surprisingly, it was found that the substituted (thiophenyl-carbonyl)imidazolidinones described in the present invention have antiviral activity.

The invention relates to compounds of formula

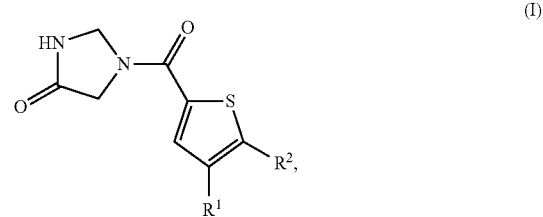

in which

R¹ represents phenyl, whereby phenyl is substituted with 1 to 3 substituents, whereby the substituents are selected independently of one another from the group consisting of halogen, hydroxy, cyano, nitro, trifluoromethyl, trifluoromethoxy, trifluoromethylthio, $(C_1-C_4)$-alkyl and $(C_1-C_4)$-alkoxy, wherein $(C_1-C_4)$-alkyl and $(C_1-C_4)$-alkoxy in turn may be substituted one to three times identically or differently with radicals selected from the group consisting of halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocyclyl, whereby the last-mentioned cycloalkyl and heterocyclyl radicals in turn may each be substituted up to three times identically or differently with halogen, cyano, $(C_1-C_4)$-alkyl, trifluoromethyl, hydroxy, $(C_1-C_4)$-alkoxy, trifluoromethoxy, oxo, amino, mono-$(C_1-C_4)$-alkylamino and di-$(C_1-C_4)$-alkylamino, and R² represents phenyl, whereby phenyl is substituted with 1 to 3 substituents, whereby the substituents are selected independently of one another from the group consisting of halogen, hydroxy, cyano, nitro, trifluoromethyl, trifluoromethoxy, trifluoromethylthio, $(C_1-C_4)$-alkyl and $(C_1-C_4)$-alkoxy, wherein $(C_1-C_4)$-alkyl and $(C_1-C_4)$-alkoxy in turn may be substituted one to three times identically or differently with radicals selected from the group consisting of halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocyclyl, whereby the last-mentioned cycloalkyl and heterocyclyl radicals in turn may each be substituted up to three times identically or differently with halogen, cyano, $(C_1-C_4)$-alkyl, trifluoromethyl, hydroxy, $(C_1-C_4)$-alkoxy, trifluoromethoxy, oxo, amino, mono-$(C_1-C_4)$-alkylamino and di-$(C_1-C_4)$-alkylamino, and the salts thereof, the solvates thereof and the solvates of the salts thereof.

Compounds of the invention are the compounds of formulae (I) and (Ia) and the salts, solvates and solvates of the salts thereof, as well as the compounds which are encompassed by formulae (I) and (Ia) and are mentioned hereinafter as exemplary embodiment(s), and the salts, solvates and solvates of the salts thereof, insofar as the compounds encompassed by formulae (I) and (Ia) and mentioned hereinafter are not already salts, solvates and solvates of the salts.

The compounds of the invention may, depending on their structure, exist in stereoisomeric forms (enantiomers, diastereomers). The invention therefore encompasses the enantiomers or diastereomers and respective mixtures thereof. The stereoisomerically uniform constituents can be isolated in a known manner from such mixtures of enantiomers and/or diastereomers.

If the compounds of the invention may occur in tautomeric forms, the present invention encompasses all tautomeric forms.

Salts preferred for the purposes of the present invention are physiologically acceptable salts of the compounds of the invention. Also encompassed however are salts which are themselves not suitable for pharmaceutical applications but can be used for example for the isolation or purification of the compounds of the invention.

Physiologically acceptable salts of the compounds of the invention include acid addition salts of mineral acids, carboxylic acids and sulfonic acids, e.g., salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases such as, by way of example and preferably, alkali metal salts (e.g., sodium and potassium salts), alkaline earth metal salts (e.g., calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates for the purposes of the invention refer to those forms of the compounds of the invention which in the solid or liquid state form a complex by coordination with solvent molecules. Hydrates are a specific form of solvates in which the coordination takes place with water.

In the context of the present invention, the substituents have the following meaning, unless specified otherwise:

Alkyl and the alkyl moieties in alkoxy and alkoxycarbonyl represent straight-chain or branched alkyl and include, unless indicated otherwise, $(C_1-C_6)$-alkyl, in particular $(C_1-C_4)$-alkyl such as, for example, methyl, ethyl, propyl, isopropyl, butyl, isobutyl.

Alkoxy for the purpose of the invention represents preferably a straight-chain or branched alkoxy radical in particular having 1 to 6, 1 to 4 or 1 to 3 carbon atoms. A straight-chain or branched alkoxy radical having 1 to 3 carbon atoms is preferred. Mention may be made by way of example and preferably of: methoxy, ethoxy, n-propoxy, isopropoxy, t-butoxy, n-pentoxy and n-hexoxy.

Alkoxycarbonyl represents by way of example and preferably methoxycarbonyl, ethoxycarbonyl, n-propoxycarbonyl, isopropoxycarbonyl, t-butoxycarbonyl, n-pentoxycarbonyl and n-hexoxycarbonyl.

Heterocyclyl represents a monocyclic heterocyclic radical having 4 to 7, preferably 5 to 6, ring atoms and up to 3, preferably up to 2, heteroatoms and/or hetero groups from the series N, O, S, SO, $SO_2$, whereby a nitrogen atom can also form an N-oxide. The heterocycle may be saturated or partly unsaturated. Preference is given to 5- to 7-membered monocyclic saturated heterocycles having up to two heteroatoms from the series O, N and S, by way of example and preferably 1,4-oxazepanyl, oxetan-3-yl, pyrrolidin-1-yl, pyrrolidin-2-yl, pyrrolidin-3-yl, tetrahydrofuranyl, tetrahydrothienyl, pyranyl, 1,3-thiazolidinyl, piperidin-1-yl, piperidin-2-yl, piperidin-3-yl, piperidin-4-yl, thiopyranyl, morpholin-2-yl, morpholin-3-yl, morpholin-4-yl, thiomorpholin-2-yl, thiomorpholin-3-yl, thiomorpholin-4-yl, perhydroazepinyl, piperazin-1-yl, piperazin-2-yl.

Halogen represents fluorine, chlorine, bromine or iodine, with preference for fluorine and chlorine, unless indicated otherwise.

Mono-$(C_1-C_4)$-alkylamino for the purpose of the invention represents an amino group having a straight-chain or branched alkyl substituent which comprises 1 to 4 carbon atoms. Mention may be made by way of example and preferably of: methylamino, ethylamino, n-propylamino, isopropylamino, n-butylamino, tert-butylamino, n-pentylamino and n-hexylamino.

Di-$(C_1-C_4)$-alkylamino for the purpose of the invention represents an amino group having two identical or different straight-chain or branched alkyl substituents which each comprise 1 to 4 carbon atoms. Mention may be made by way of example and preferably of: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino, N-methyl-N-n-pentylamino and N-n-hexyl-N-methylamino.

$(C_3-C_7)$-Cycloalkyl for the purpose of the invention represents a monocyclic saturated carbocycle having 3 to 7 or 3 to 6 ring carbon atoms. Mention may be made by way of example and preferably of: cyclopropyl, cyclobutyl, cyclopentyl, cyclohexyl and cycloheptyl.

The radical definitions listed above and indicated in general or in preferred ranges apply both to the final products of formulae (I) and (Ia) and correspondingly to the starting materials and intermediates required for the preparation in each case.

The radical definitions indicated specifically in the respective combinations or preferred combinations of radicals are replaced irrespective of the particular combinations of radicals indicated as desired also by radical definitions of other combinations.

The invention also relates to compounds of formula (I) in which
$R^1$ represents phenyl,
whereby phenyl is substituted with 1 to 2 substituents, whereby the substituents are selected independently of one another from the group consisting of halogen, hydroxy, cyano, nitro, trifluoromethyl, trifluoromethoxy, trifluoromethylthio, $(C_1-C_4)$-alkyl and $(C_1-C_4)$-alkoxy, and
$R^2$ represents phenyl,
whereby phenyl is substituted with 1 to 2 substituents, whereby the substituents are selected independently of one another from the group consisting of halogen, hydroxy, cyano, nitro, trifluoromethyl, trifluoromethoxy, trifluoromethylthio, $(C_1-C_4)$-alkyl and $(C_1-C_4)$-alkoxy,
wherein
$(C_1-C_4)$-alkoxy in turn may be substituted one to three times identically or differently with radicals selected from the group consisting of halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocyclyl,
whereby the last-mentioned cycloalkyl and heterocyclyl radicals in turn may each be substituted up to three times identically or differently with halogen, cyano, $(C_1-C_4)$-alkyl, trifluoromethyl, hydroxy, $(C_1-C_4)$-alkoxy, trifluoromethoxy, oxo, amino, mono-$(C_1-C_4)$-alkylamino and di-$(C_1-C_4)$-alkylamino,
and the salts thereof, the solvates thereof and the solvates of the salts thereof.

The invention also relates to compounds of formula (I) in which
$R^1$ represents phenyl,
whereby phenyl is substituted with 1 to 2 substituents, whereby the substituents are selected independently of one another from the group consisting of halogen, cyano, trifluoromethyl, methyl and methoxy, and
$R^2$ represents phenyl,
whereby phenyl is substituted with 1 to 2 substituents, whereby the substituents are selected independently of one another from the group consisting of halogen, cyano, trifluoromethyl, trifluoromethoxy, methyl and $(C_1-C_3)$-alkoxy,
and the salts thereof, the solvates thereof and the solvates of the salts thereof.

The invention also relates to compounds of formula (I) in which
$R^1$ represents phenyl,
whereby phenyl is substituted with 1 to 2 substituents, whereby the substituents are selected independently of one another from the group consisting of halogen and cyano, and
$R^2$ represents phenyl,
whereby phenyl is substituted with 1 to 2 substituents, whereby the substituents are selected independently of one another from the group consisting of halogen, cyano and trifluoromethyl,
and the salts thereof, the solvates thereof and the solvates of the salts thereof.

The invention also relates to compounds of formula (I) in which
$R^1$ represents phenyl,
whereby phenyl is substituted with 1 to 2 substituents, whereby the substituents are selected independently of one another from the group consisting of halogen and cyano, and
$R^2$ represents phenyl,
whereby phenyl is substituted with 1 to 2 substituents, whereby the substituents are selected independently of one another from the group consisting of halogen and cyano,
and the salts thereof, the solvates thereof and the solvates of the salts thereof.

The invention also relates to compounds of formula

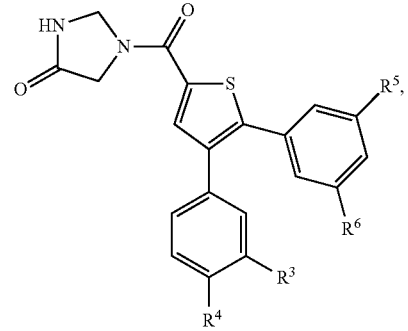

(Ia)

in which
$R^3$ represents halogen or cyano,
$R^4$ represents hydrogen or halogen,
$R^5$ represents halogen, cyano or trifluoromethyl, and
$R^6$ represents hydrogen or halogen,
and the salts thereof, the solvates thereof and the solvates of the salts thereof.

The invention also relates to compounds of formula (Ia) in which
$R^3$ represents halogen or cyano,
$R^4$ represents hydrogen or halogen,
$R^5$ represents halogen or cyano, and
$R^6$ represents hydrogen or halogen,
and the salts thereof, the solvates thereof and the solvates of the salts thereof.

The invention also relates to compounds of formula (Ia) in which
$R^3$ represents fluorine, chlorine or cyano,
$R^4$ represents hydrogen, chlorine or fluorine,
$R^5$ represents fluorine, chlorine or cyano, and
$R^6$ represents hydrogen, chlorine or fluorine,
and the salts thereof, the solvates thereof and the solvates of the salts thereof.

The invention also relates to compounds of formula (Ia) in which
$R^3$ represents chlorine or cyano,
$R^4$ represents hydrogen or fluorine,
$R^5$ represents chlorine or cyano, and
$R^6$ represents hydrogen or fluorine,
and the salts thereof, the solvates thereof and the solvates of the salts thereof.

The invention also relates to compounds of formula (Ia) in which
$R^3$ represents chlorine or cyano,
$R^4$ represents fluorine,
$R^5$ represents chlorine or cyano, and
$R^6$ represents fluorine,
and the salts thereof, the solvates thereof and the solvates of the salts thereof.

The invention also relates to compounds of formula (Ia) in which
$R^3$ represents chlorine or cyano,
$R^4$ represents fluorine,
$R^5$ represents chlorine or cyano, and
$R^6$ represents hydrogen,
and the salts thereof, the solvates thereof and the solvates of the salts thereof.

The invention also relates to compounds of formula (Ia) in which
$R^3$ represents chlorine or cyano,
$R^4$ represents hydrogen,
$R^5$ represents chlorine or cyano, and
$R^6$ represents hydrogen,
and the salts thereof, the solvates thereof and the solvates of the salts thereof.

The invention also relates to compounds of formula (Ia) in which
$R^3$ represents chlorine or cyano,
$R^4$ represents hydrogen,
$R^5$ represents chlorine or cyano, and
$R^6$ represents fluorine,
and the salts thereof, the solvates thereof and the solvates of the salts thereof.

The invention furthermore relates to a method for preparing the compounds of formulae (I) and (Ia) whereby compounds of formula

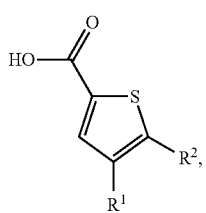

(II)

in which
$R^1$ and $R^2$ have the meaning given above,
are reacted with imidazolidin-4-one or with a salt of imidazolidin-4-one.

The reaction generally takes place in inert solvents in the presence of a dehydrating agent, where appropriate in the presence of a base, preferably in a temperature range of from −30° C. to 50° C. under atmospheric pressure.

Examples of inert solvents are halogenated hydrocarbons such as dichloromethane or trichloromethane, hydrocarbons such as benzene or toluene, nitromethane, tetrahydrofuran, 1,4-dioxane, dimethylformamide or acetonitrile. It is also possible to use mixtures of the solvents. Particular preference is given to dichloromethane, dimethylformamide, tetrahydrofuran or toluene.

Bases are, for example, alkali metal carbonates, such as, for example, sodium carbonate or potassium carbonate or sodium bicarbonate or potassium bicarbonate, or organic bases such as trialkylamines, for example triethylamine, N-methylmorpholine, N-methylpiperidine, 4-dimethylaminopyridine or diisopropylethylamine.

Examples for suitable dehydrating agents in this connection are carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide) or carbonyl compounds such as carbonyldiimidazol, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanphosphonic anhydride, or isobutyl chloroformate, or bis-(2-oxo-3-oxazolidinyl)phosphoryl chloride, or O-(benzotriazol-1-yl)-N,N,N',N'-tetramethyluroniumhexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol-1-yloxytris(pyrrolidino)phosphonium hexafluorophosphate (PyBOP), or N-hydroxysuccinimide, or mixtures of these, with bases.

The condensation is preferably carried out with PyBOP, TBTU or with EDC in the presence of HOBt.

In an alternative method, the compounds of formula (II) can be reacted initially with thionyl chloride and in the second step with imidazolidin-4-one or a salt of imidazolidin-4-one in the presence of a base such as, for example triethylamine The compounds of formulae (I) and (Ia) prepared by the methods described above optionally carry protecting groups which may be removed under conditions known to the person skilled in the art to obtain further compounds of formulae (I) and (Ia).

The compounds of formula (II) are known or can be prepared by hydrolyzing the ester in compounds of formula

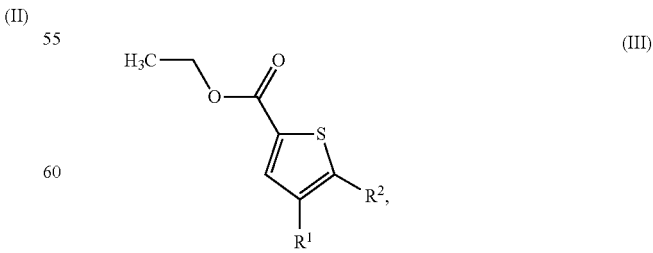

(III)

in which
$R^1$ and $R^2$ have the meaning given above,
with a base.

The hydrolysis of the ester with a base generally takes place in inert solvents, preferably in a temperature range of from room temperature to the reflux of the solvent under atmospheric pressure.

Examples of bases are alkali metal hydroxides such as sodium hydroxide, lithium hydroxide or potassium hydroxide, or alkali metal carbonates such as cesium carbonate, sodium carbonate or potassium carbonate; preference is given to lithium hydroxide, potassium hydroxide or sodium hydroxide.

Examples of inert solvents are halogenated hydrocarbons such as methylene chloride, trichloromethane, carbon tetrachloride, trichloroethane, tetrachloroethane, 1,2-dichloroethane or trichloroethylene, ethers such as diethyl ether, methyl tert-butyl ether, 1,2-dimethoxyethane, 1,4-dioxane, tetrahydrofuran, glycol dimethyl ether or diethylene glycol dimethyl ether, alcohols such as methanol, ethanol, n-propanol, isopropanol, n-butanol or tert-butanol, hydrocarbons such as benzene, xylene, toluene, hexane, cyclohexane or mineral oil fractions, or other solvents such as dimethylformamide, dimethylacetamide, dimethyl sulfoxide, acetonitrile or pyridine, or water, or mixtures of solvents. Preferred solvents are 1,4-dioxane, tetrahydrofuran and/or methanol. Preference is given to lithium hydroxide in tetrahydrofuran- or 1,4-dioxane-water mixtures or potassium hydroxide in methanol.

The compounds of formula (III) are known or can be prepared by reacting compounds of formula

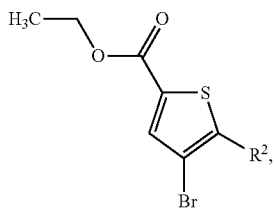

(IV)

in which

R² has the meaning given above, under Suzuki coupling conditions with compounds of formula

R¹-Q (V), in which

R¹ has the meaning given above and

Q represents —B(OH)₂, a boronic acid ester, preferably boronic acid pinacol ester, or —BF₃⁻K⁺.

The Suzuki couplings generally take place in inert solvents, in the presence of a catalyst, where appropriate in the presence of an additional reagent, preferably in a temperature range of from room temperature to 130° C. under atmospheric pressure.

Catalysts are, for example, palladium catalysts customary for Suzuki reaction conditions; preference is given to catalysts such as, for example, dichlorobis(triphenylphosphine)palladium, tetrakistriphenylphosphinepalladium(0), palladium(II) acetate, palladium(II) acetate/triscyclohexylphosphine or bis-(diphenylphosphaneferrocenyl)palladium(II) chloride or palladium(II) acetate with a ligand such as dicyclohexyl[2',4',6'-tri(propan-2-yl)biphenyl-2-yl]phosphane.

Examples of additional reagents are potassium acetate, cesium carbonate, potassium carbonate or sodium carbonate, potassium tert-butoxide, cesium fluoride or potassium phosphate; preference is given to additional reagents such as, for example, potassium acetate and/or an aqueous sodium carbonate solution.

Examples of inert solvents are ethers such as dioxane, tetrahydrofuran or 1,2-dimethoxyethane, hydrocarbons such as benzene, xylene or toluene, or carboxamides such as dimethylformamide or dimethylacetamide, alkyl sulfoxides such as dimethyl sulfoxide, or N-methylpyrrolidone, or mixtures of the solvents with alcohols such as methanol or ethanol and/or water; preference is given to 1,2-dimethoxyethane.

The compounds of the formula (V) are known or can be synthesized by known methods from the corresponding starting materials.

The compounds of formula (IV) are known or can be prepared by reacting the compound of formula

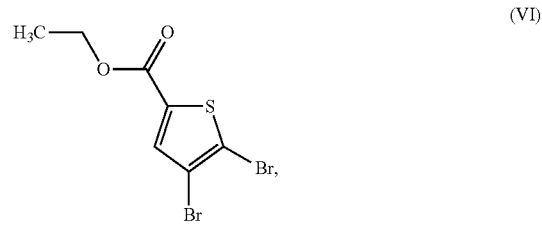

(VI)

under the Suzuki coupling conditions described above with compounds of formula

R²-Q (VII), in which

R¹ has the meaning given above and

Q represents —B(OH)₂, a boronic acid ester, preferably boronic acid pinacol ester, or —BF₃⁻K⁺.

The compounds of the formulae (VI) and (VII) are known or can be synthesized by known methods from the corresponding starting materials.

The invention furthermore relates to a method for preparing the compounds of formulae (I) and (Ia) whereby compounds of formula

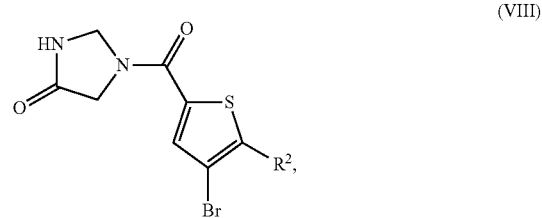

(VIII)

in which

R² has the meaning given above are reacted under the Suzuki coupling conditions described above with compounds of formula

R¹-Q (V), in which

R¹ has the meaning given above and

Q represents —B(OH)₂, a boronic acid ester, preferably boronic acid pinacol ester, or —BF₃⁻K⁺.

The compounds of formula (VIII) are known or can be prepared by reacting compounds of formula

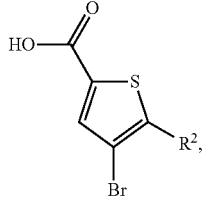
(IX)

in which

R² has the meaning given above, with imidazolidin-4-one or with a salt of imidazolidin-4-one, in analogy to the conversion, described above, of (II) into (I) or (Ia).

The compounds of the formula (IX) are known or can be prepared by hydrolyzing the ester in compounds of formula

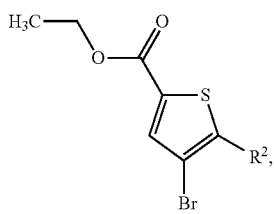
(IV)

in which

R² has the meaning given above, using a base, as described above for the conversion of (III) into (II).

The invention furthermore relates to a method for preparing the compounds of formulae (I) and (Ia) whereby compounds of formula

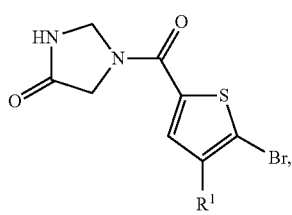
(X)

in which

R¹ has the meaning given above are reacted under the Suzuki coupling conditions described above with compounds of formula

R²-Q                                                (VII), in which

R² has the meaning given above and

Q represents —B(OH)₂, a boronic acid ester, preferably boronic acid pinacol ester, or —BF₃⁻K⁺.

The compounds of formula (X) are known or can be prepared by reacting compounds of formula

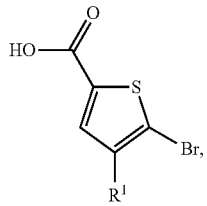
(XI)

in which

R¹ has the meaning given above with imidazolidin-4-one or a salt of imidazolidin-4-one, in analogy to the conversion, described above, of (II) into (I) or (Ia).

The compounds of the formula (XI) are known or can be prepared by hydrolyzing the ester in compounds of formula

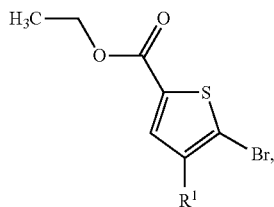
(XII)

in which

R¹ has the meaning given above, using a base, as described above for the conversion of (III) into (II).

The compounds of the formula (XII) are known or can be prepared by brominating compounds of formula

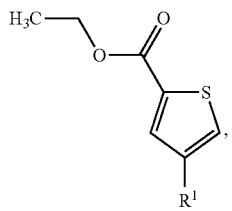
(XIII)

in which

R¹ has the meaning given above.

Examples of inert solvents for the bromination are halogenated hydrocarbons such as dichloromethane, trichloromethane, carbon tetrachloride, trichloroethane, tetrachloroethane, 1,2-dichloroethane or trichloroethylene, ethers such as diethyl ether, dioxane, tetrahydrofuran, glycol dimethyl ether or diethylene glycol dimethyl ether, hydrocarbons such as hexane or cyclohexane, organic carboxylic acids such as acetic acid, or other solvents such as ethyl acetate, dimethylformamide or dimethylsulfoxide. It is also possible to use mixtures of the solvents mentioned. Preference is given to acetic acid, diethyl ether, dioxane, tetrahydrofuran, ethyl acetate, trichloromethane and/or carbon tetrachloride.

Suitable brominating agents are the customary inorganic or organic reagents. These preferably include bromine, N-bromosuccinimide, copper dibromide, pyridine hydrotribromide, dimethylbenzylammonium tribromide or phenyltrimethylammonium tribromide. Particular preference is given to bromine and copper dibromide.

The bromination is generally carried out in a temperature range of from −20° C. to 150° C., preferably from 0° C. to 80° C. The reaction can be carried out under atmospheric, elevated or reduced pressure (for example from 0.5 to 5 bar). In general, the bromination is carried out under atmospheric pressure.

The compounds of the formula (XII) are known or can be prepared by reacting the compound of formula

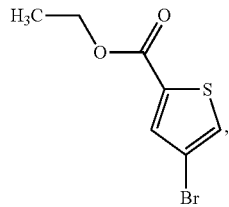
(XIV)

under the Suzuki coupling conditions described above with compounds of formula

R¹-Q  (V), in which

R¹ has the meaning given above and

Q represents —B(OH)$_2$, a boronic acid ester, preferably boronic acid pinacol ester, or —BF$_3^-$K$^+$.

The compound of formula (XIV) is known or can be synthesized by known methods.

The preparation of the compounds according to the invention can be illustrated by the synthesis schemes below.

Synthesis scheme I:

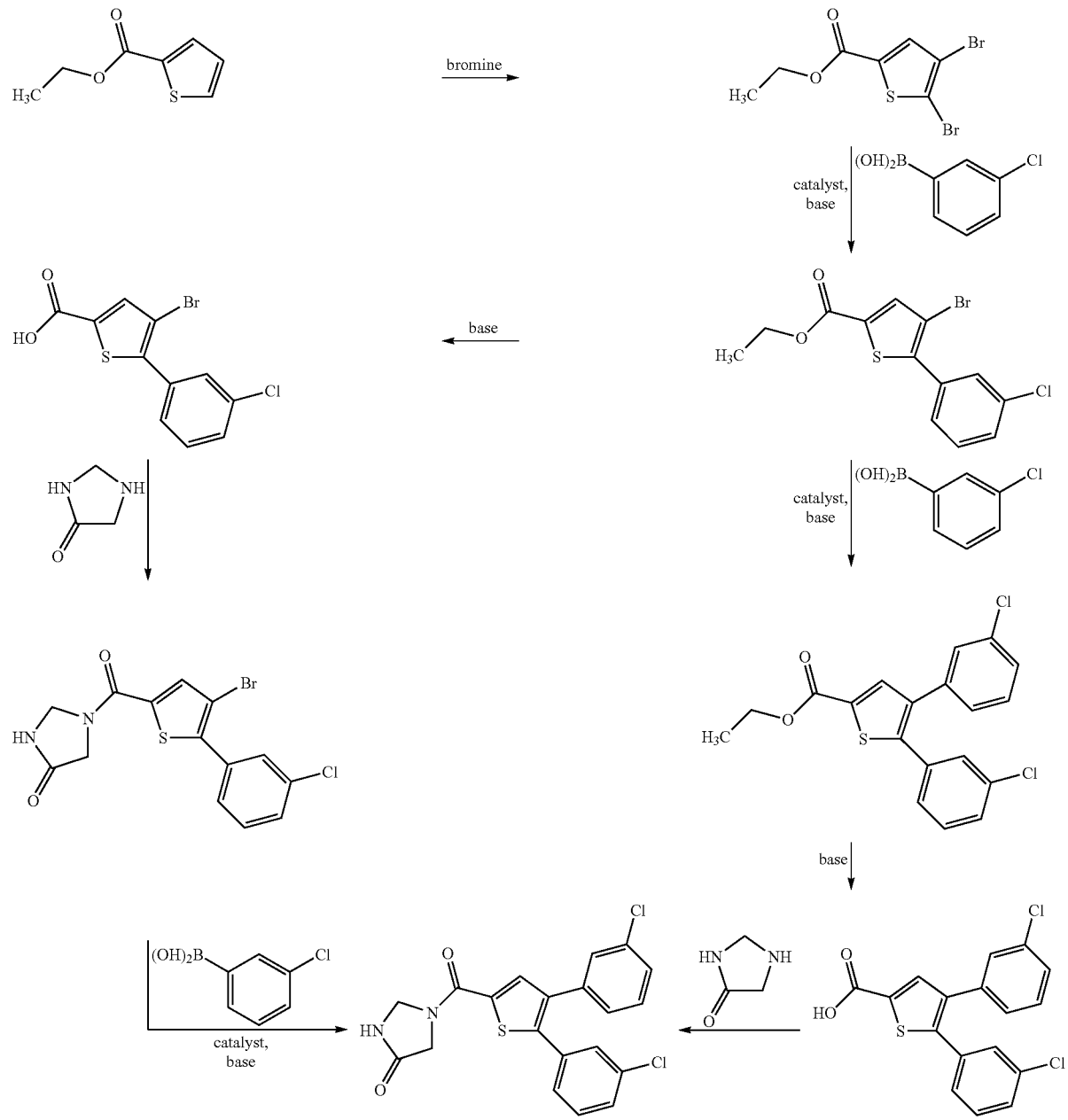

Synthesis scheme II:

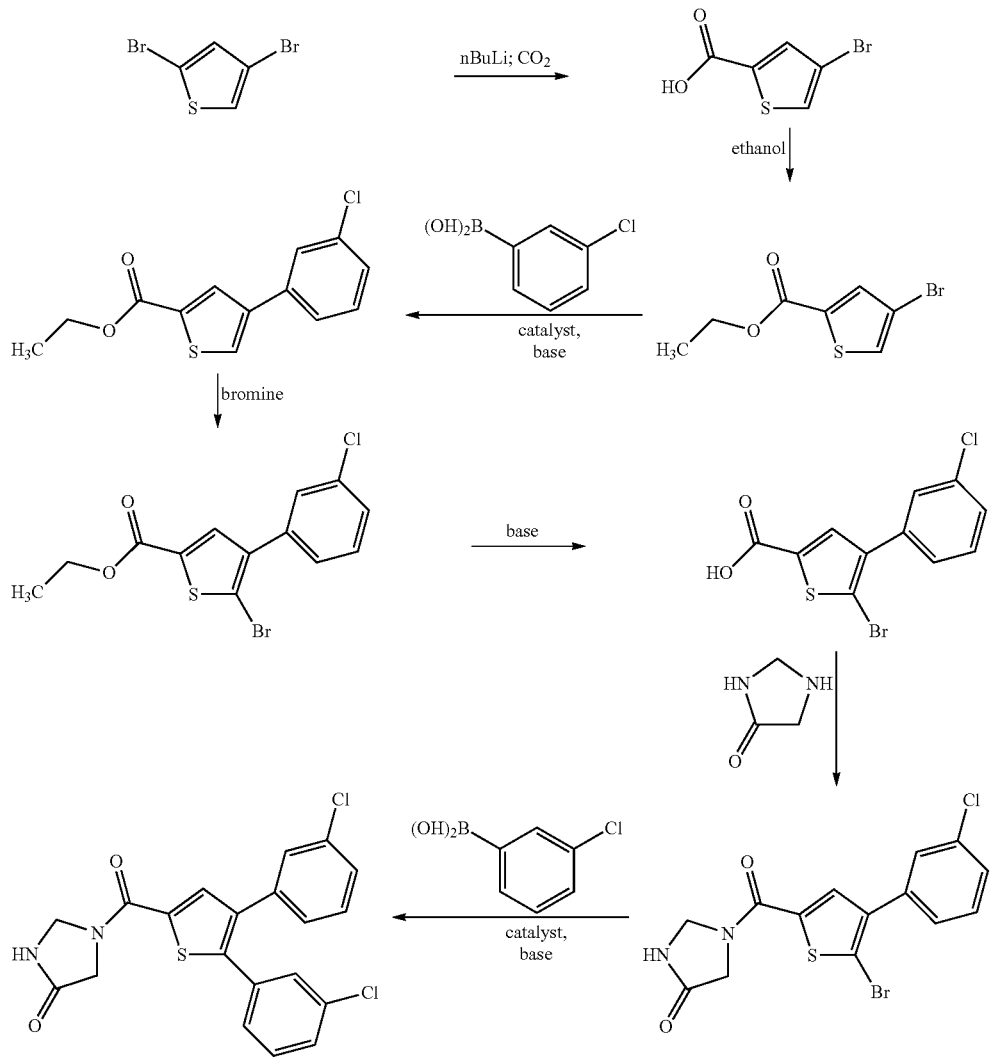

The compounds of the invention show a valuable range of pharmacological effects which could not have been predicted.

They are therefore suitable for use as medicaments for the treatment and/or prophylaxis of diseases in humans and animals.

The compounds of the present invention are distinguished in particular by an advantageous range of antiretroviral effects.

The present invention further relates to the use of the compounds of the invention for the treatment and/or prophylaxis of diseases caused by retroviruses, especially HI viruses.

The present invention further relates to the use of the compounds of the invention for the treatment and/or prophylaxis of diseases, especially of the aforementioned diseases.

The present invention further relates to the use of the compounds of the invention for the manufacture of a medicament for the treatment and/or prophylaxis of diseases, especially of the aforementioned diseases.

The present invention further relates to a method for the treatment and/or prophylaxis of diseases, especially of the aforementioned diseases, using a therapeutically effective amount of the compounds of the invention.

Examples of areas of indication in human medicine which may be mentioned are:

1.) The treatment and prophylaxis of human retroviral infections

2.) The treatment and prophylaxis of infections and diseases (AIDS) caused by HIV-1 (human immunodeficiency virus; formerly called HTLV III/LAV) and HIV-2 and the stages associated therewith, such as ARC (AIDS related complex) and LAS (lymphadenopathy syndrome), as well as the immunodeficiency and encephalopathy caused by this virus.

3.) The treatment of HIV infections caused by mono-, poly- or multiresistant HI viruses.

The expression resistant HI viruses means for example viruses with resistances to nucleosidic RT inhibitors (NRTI), non-nucleosidic RT inhibitors (NNRTI) or protease inhibitors (PI) or viruses with resistances to other principles of action, e.g., T20 (fusion inhibitors).

4.) The treatment or prophylaxis of the AIDS-carrier state.

5.) The treatment or prophylaxis of an HTLV-I or HTLV-II infection.

Examples of indications in veterinary medicine which may be mentioned are:

Infections with
a) Maedi-visna (in sheep and goats)
b) progressive pneumonia virus (PPV) (in sheep and goats)
c) caprine arthritis encephalitis virus (in sheep and goats)
d) zwoegerziekte virus (in sheep)
e) infectious anaemia virus (of horses)
f) infections caused by the feline leukaemia virus
g) infections caused by the feline immunodeficiency virus (FIV)
h) infections caused by the simian immunodeficiency virus (SIV)

Preference is given from the area of indications in human medicine to items 2, 3 and 4 detailed above.

The substances are particularly suitable for controlling HI viruses showing resistances to known non-nucleosidic inhibitors of the reverse transcriptase, such as, for example, efavirenz or nevirapine.

The present invention further relates to medicaments comprising at least one compound of the invention and at least one or more further active ingredients, in particular for the treatment and/or prophylaxis of the aforementioned diseases.

The compounds of the invention can also, especially in items 2, 3 and 4 detailed above, advantageously be employed as components of a combination therapy with one or more other compounds which are active in these areas of application. These compounds can for example be employed in combination with effective doses of substances having antiviral activity based on the principles of action detailed below:

HIV protease inhibitors; examples which may be mentioned are: saquinavir, indinavir, ritonavir, nelfinavir, amprenavir, lopinavir, atazanavir, fosamprenavir, tipranavir, darunavir;

nucleosidic, nucleotidic and non-nucleosidic inhibitors of the HIV reverse transcriptase; examples which may be mentioned are: zidovudine, lamivudine, didanosine, zalcitabine, stavudine, lamivudine, abacavir, tenofovir, adefovir, emtricitabine, amdoxovir, apricitabine, racivir, nevirapine, delavirdine, efavirenz, etravirine, rilpivirine, UK-453,061;

HIV integrase inhibitors, examples which may be mentioned are: raltegravir, elvitegravir;

HIV fusion inhibitors; an example which may be mentioned is: enfuvirtide;

inhibitors of the CXCR4/CCR5/gp120 interaction; examples which may be mentioned are: maraviroc, vicriviroc, INCB009471, AMD-070;

inhibitors of the polyprotein maturation; an example which may be mentioned is: bevirimat.

This selection is intended to serve to illustrate the possible combinations but not to restrict to the examples detailed here. In principle, every combination of the compounds of the invention with substances having antiviral activity is to be considered as within the scope of the invention.

The compounds of the invention may act systemically and/or locally. They can for this purpose be administered in a suitable way, such as, for example, orally, parenterally, pulmonarily, nasally, sublingually, lingually, buccally, rectally, dermally, transdermally, conjunctivally, otically or as an implant or stent.

For these administration routes the compounds of the invention can be administered in suitable administration forms.

Suitable for oral administration are administration forms which function according to the prior art and deliver the compounds of the invention rapidly and/or in a modified manner, and which contain the compounds of the invention in crystalline and/or amorphized and/or dissolved form, such as, for example, tablets (uncoated or coated tablets, for example having coatings which are resistant to gastric juice or dissolve with a delay or are insoluble and control the release of the compound of the invention), tablets or films/wafers which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g., intravenous, intraarterial, intracardiac, intraspinal or intralumbar) or with inclusion of an absorption (e.g., intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other administration a routes are, for example, pharmaceutical forms for inhalation (inter alia powder inhalers, nebulizers), nasal drops, solutions, sprays; tablets, films/wafers or capsules, for lingual, sublingual or buccal administration, suppositories, preparations for ears or eyes, vaginal capsules, aqueous suspensions (lotions, shaking mixtures), lipophilic suspensions, ointments, creams, transdermal therapeutic systems (such as for example patches), milk, pastes, foams, dusting powders, implants or stents.

The compounds of the invention can be converted into the stated administration forms. This can take place in a manner known per se by mixing with inert, non-toxic, pharmaceutically acceptable excipients. These excipients include inter alia carriers (for example microcrystalline cellulose, lactose, mannitol), solvents (e.g., liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g., antioxidants such as, for example, ascorbic acid), colors (e.g., inorganic pigments such as, for example, iron oxides) and taste and/or odor corrigents.

The present invention further relates to medicaments which comprise at least one compound of the invention, usually together with one or more inert, non-toxic, pharmaceutically acceptable excipients, as well as to their use for the aforementioned purposes.

It has generally proved to be advantageous both in human and in veterinary medicine to administer the active ingredient(s) of the invention in total amounts of from 0.1 to 200 mg/kg, preferably 1 to 100 mg/kg, of body weight every 24 hours, where appropriate in the form of a plurality of single doses, to achieve the desired result. A single dose preferably comprises the active ingredient(s) in amounts of from 1 to 80 mg/kg, in particular 1 to 30 mg/kg, of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. In the case of an administration of larger amounts, it may be advisable to distribute these in a plurality of single doses over the day.

The percentage data in the following tests and examples are, unless indicated otherwise, percentages by weight; parts are parts by weight. Solvent ratios, dilution ratios and concentration data of liquid/liquid solutions are based in each case on volume. The statement "w/v" means "weight/volume". Thus, for example, "10% w/v" means: 100 ml of solution or suspension contain 10 g of substance.

DESCRIPTION OF PREFERRED EMBODIMENTS

A) Examples

Abbreviations:

| | |
|---|---|
| aq. | aqueous, aqueous solution |
| conc. | concentrated |
| DCI | direct chemical ionization (in MS) |
| DMA | N,N-dimethylacetamide |
| DMF | N,N-dimethylformamide |
| DMSO | dimethyl sulfoxide |
| EDC | N'-(3-dimethylaminopropyl)-N-ethylcarbodiimide × HCl |
| eq. | equivalent(s) |
| ESI | electrospray ionization (in MS) |
| h | hour(s) |
| HATU | O-(7-azabenzotriazol-1-yl)-N,N,N',N'-tetramethyluronium hexafluorophosphate |
| HPLC | high pressure, high performance liquid chromatography |
| LC-MS | coupled liquid chromatography-mass spectrometry |
| min | minute(s) |
| MS | mass spectrometry |
| NMR | nuclear magnetic resonance spectroscopy |
| PyBOP | benzotriazol-1-yloxytris(pyrrolidino)phosphonium hexafluorophosphate |
| $R_t$ | retention time (in HPLC) |
| RT | room temperature |
| TBTU | O-(benzotriazol-1-yl)-N,N,N',N'-tetramethyluronium tetrafluoroborate |
| TFA | trifluoroacetic acid |
| THF | tetrahydrofuran |
| TMOF | trimethyl orthoformate |

LC-MS/GC-MS Methods:

Method 1:

MS instrument type: Micromass ZQ; HPLC instrument type: HP 1100 Series; UV DAD; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 2:

Instrument: Micromass Quattro LCZ with HPLC Agilent™ Series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm Method 3:

MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 4:

Instrument: Micromass Quattro LCZ with HPLC Agilent™ Series 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A →2 min 65% A→4.5 min 5% A→6 min 5% A; flow rate: 2 ml/min; oven: 40° C.; UV detection: 208-400 nm.

Method 5:

Instrument: Micromass QuattroPremier with Waters HPLC Acquity; column: Thermo Hypersil GOLD 1.9μ 50 mm×1 mm; eluent A: 1 l of water+0.5 ml of 50% formic acid, eluent B: 1 l of acetonitrile+0.5 ml of 50% formic acid; gradient: 0.0 min 90% A→0.1 min 90% A→1.5 min 10% A→2.2 min 10% A; oven: 50° C.; flow rate: 0.33 ml/min; UV detection: 210 nm.

Method 6:

MS instrument type: Waters ZQ; HPLC instrument type: Waters Alliance 2795; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 210 nm.

Method 7:

MS instrument type: Micromass ZQ; HPLC instrument type: Waters Alliance 2795;

column: Phenomenex Synergi 2.5μ MAX-RP 100A Mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 8:

Instrument: Micromass Quattro LCZ with HPLC Agilent™ Series 1100; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 9:

Instrument: Micromass Quattro LCZ with HPLC Agilent™ Series 1100; column: Phenomenex Synergi 2.5μ MAX-RP 100A Mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm Method 10:

MS instrument type: Waters (Micromass) Quattro Micro; HPLC instrument type: Agilent™ 1100 Series; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 11:

Instrument: Micromass GCT, GC6890; column: Restek RTX-35, 15 m×200 μm×0.33 μm; constant helium flow rate: 0.88 ml/min; oven: 70° C.; inlet: 250° C.; gradient: 70° C., 30° C./min→310° C. (hold for 3 min).

Method 12:

Instrument: Micromass GCT, GC6890; column: Restek RTX-35, 15 m×200 μm×0.33 μm; constant helium flow: 0.88

Starting Materials and Intermediates

Example 1A

N²-Benzylglycinamide

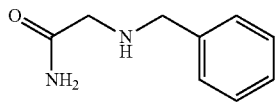 [SMILES: NC(=O)CNCc1ccccc1]

Under argon, 44.2 g (0.40 mol) of glycinamide hydrochloride are provided in 2.2 l of dichloromethane at room temperature, 112 ml (0.80 mol) of triethylamine are added and the mixture is stirred at room temperature overnight. 42.5 g (0.40 mol) of benzaldehyde are then added, and the reaction mixture is heated under reflux on a water separator overnight. The mixture is concentrated, the residue is dissolved in 400 ml of tetrahydrofuran/methanol (1:1), 16.7 g (0.44 mol) of sodium borohydride are added in portions at 0° C. and the mixture is stirred at room temperature for two days. The suspension is filtered with suction and the filtrate is concentrated and dried under high vacuum. The residue is triturated with ethyl acetate, the precipitate is filtered off, the filtrate is concentrated and the residue is stirred in toluene overnight. After Filtration of the solid and subsequent drying under high vacuum 56.5 g (84% of theory) of the title compound are obtained.

¹H-NMR (400 MHz, DMSO-$d_6$): δ=7.36-7.28 (m, 4H), 7.27-7.19 (m, 1H), 3.66 (d, 2H), 3.02 (d, 2H).

LC-MS (Method 10): $R_t$=0.40 min; MS (ESIpos): m/z=165 [M+H]⁺.

Example 2A

1-Benzyl-3-(hydroxymethyl)imidazolidin-4-one

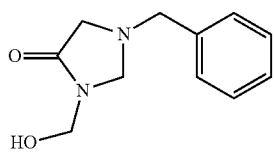 [SMILES: O=C1CN(Cc2ccccc2)CN1CO]

172 ml (6.20 mol) of a 37% formaldehyde solution are added to 56.5 g (0.34 mol) of the compound from Example 1A, and the mixture is heated under reflux for 30 minutes. The reaction mixture is extracted with dichloromethane and the combined organic phases are dried over sodium sulfate, filtered and concentrated. 74.5 g (100% of theory) of the title compound are obtained.

LC-MS (Method 5): $R_t$=0.51 min; MS (ESIpos): m/z=207 [M+H]⁺.

Example 3A

1-Benzylimidazolidin-4-one trifluoroacetate

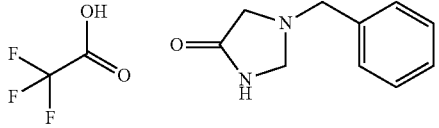 [SMILES: O=C(O)C(F)(F)F ; O=C1CN(Cc2ccccc2)CN1]

At 150° C., 74.5 g (0.36 mol) of the compound from Example 2A are heated under high vacuum with destillative removal of volatile reaction products for 6 h. Purification is carried out by HPLC (column: Sunfire C18 5μ, 250×20 mm; eluent: 0.2% trifluoroacetic acid-water/acetonitrile gradient). 28.4 g (27% of theory) of the title compound are obtained.

¹H-NMR (400 MHz, DMSO-$d_6$): δ=8.75 (s, 1H), 7.48-7.39 (m, 5H), 4.41 (s, 2H), 4.22 (s, 2H), 3.54 (s, 2H).

LC-MS (Method 10): $R_t$=0.94 min; MS (ESIpos): m/z=177 [M–CF₃COOH+H]⁺.

Example 4A

Imidazolidin-4-one trifluoroacetate

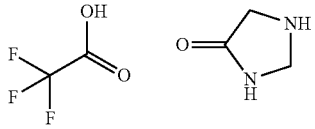

28.4 g (97.9 mmol) of the compound from Example 3A are dissolved in 750 ml of ethanol, and under argon, 4.5 g (42.3 mmol) of palladium on activated carbon (5%) are added. The mixture is hydrogenated under an atmosphere of hydrogen for 24 h. The suspension is filtered through Celite, concentrated and dried under high vacuum. 19.2 g (98% of theory) of the title compound are obtained.

¹H-NMR (400 MHz, DMSO-$d_6$): δ=10.1 (s, 2H), 8.89 (s, 1H), 4.55 (s, 2H), 3.63 (s, 2H).

GC-MS (Method 11): $R_t$=3.92 min; MS (EIpos): m/z=86 [M–CF₃COOH]⁺.

Example 5A

3-Fluoro-5-(4,4,5,5-tetramethyl-1,3,2-dioxaborolan-2-yl)benzenecarbonitrile

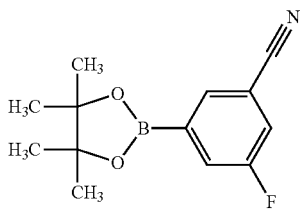 [SMILES: CC1(C)OB(c2cc(F)cc(C#N)c2)OC1(C)C]

Under argon, 3.60 g (18.0 mmol) of 3-bromo-5-fluorobenzenecarbonitrile, 5.03 g (19.8 mmol) of 4,4,4',4',5,5,5',5'-octamethyl-2,2'-bi-1,3,2-dioxaborolane and 5.30 g (54.0 mmol) of potassium acetate are provided in 72 ml of degassed 1,4-dioxane/DMSO (10/1), and 441 mg (0.54 mmol) of 1,1'-bis(diphenylphosphine)ferrocenedichloropalladium(II)/dichloromethane complex are added. The mixture is stirred at 90° C. overnight. Water is subsequently added, the phases are separated, the aqueous phase is extracted with ethyl acetate and the combined organic phases are concentrated. The crude product is purified by flash chromatography (mobile phase: cyclohexane/ethyl acetate 10:1). 4.48 g (92% of theory) of the title compound are obtained.

$^1$H-NMR (400 MHz, DMSO-$d_6$): δ=8.01 (ddd, 1H), 7.82 (s, 1H), 7.70 (ddd, 1H), 1.32 (s, 12H).

GC-MS (Method 11): $R_t$=4.94 min; MS (EIpos): m/z=247 [M]$^+$.

Example 6A

4-Bromothiophene-2-carboxylic acid

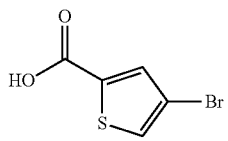

Under argon, 1.00 g (4.13 mmol) of 2,4-dibromothiophene is provided in 15 ml of diethyl ether, and the mixture is cooled to −78° C. 2.6 ml (4.13 mmol) of a 1.6N solution of n-butyl-lithium in hexane are added, and the reaction mixture is stirred for 5 minutes. The reaction mixture is added to a mixture of dry ice and 15 ml of diethyl ether and stirred for 10 minutes. The mixture is subsequently diluted with water, and the phases are separated. The aqueous phase is acidified and extracted with ethyl acetate, and the organic phase is dried over sodium sulfate, filtered and concentrated. 0.66 g (74% of theory) of the title compound are obtained.

$^1$H-NMR (400 MHz, DMSO-$d_6$): δ=13.5 (s, 1H), 8.02 (d, 1H), 7.69 (d, 1H).

LC-MS (Method 1): $R_t$=1.88 min; MS (ESIpos): m/z=207 [M+H]$^+$.

Example 7A

Ethyl 4-bromothiophene-2-carboxylate

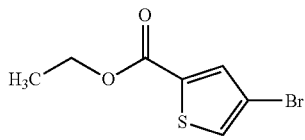

663 mg (3.20 mmol) of the compound from Example 6A are provided in 25 ml of ethanol, 0.1 ml of concentrated sulfuric acid is added and the mixture is heated under reflux overnight. After cooling to room temperature, a saturated aqueous sodium bicarbonate solution is added and the mixture is diluted with water and extracted with ethyl acetate. The organic phase is dried over sodium sulfate, filtered and concentrated. 700 mg (89% of theory) of the title compound are obtained.

$^1$H-NMR (400 MHz, DMSO-$d_6$): δ=8.07 (d, 1H), 7.78 (d, 1H), 4.30 (q, 2H), 1.30 (t, 3H).

GC-MS (Method 11): $R_t$=4.69 min; MS (EIpos): m/z=234 [M]$^+$.

Example 8A

Ethyl 4,5-dibromothiophene-2-carboxylate

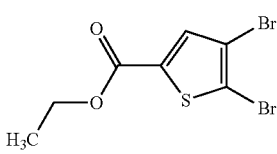

16.5 ml (320 mmol) of bromine are provided in 120 ml of acetic acid, and 10.0 g (64.0 mmol) of ethyl thiophene-2-carboxylate, dissolved in 40 ml of acetic acid, are added dropwise. The mixture is stirred at 60° C. overnight. The reaction mixture is concentrated, a saturated aqueous sodium bicarbonate solution is added to the residue and the mixture is extracted with dichloromethane. The organic phase is dried over magnesium sulfate, filtered and concentrated. The crude product is recrystallized from diethyl ether. 7.80 g (39% of theory) of the title compound are obtained.

$^1$H-NMR (400 MHz, DMSO-$d_6$): δ=7.79 (s, 1H), 4.30 (q, 2H), 1.29 (t, 3H).

GC-MS (Method 11): $R_t$=5.55 min; MS (EIpos): m/z=314 [M]$^+$.

Example 9A

Ethyl 4-bromo-5-(3-chloro-5-fluorophenyl)thiophene-2-carboxylate

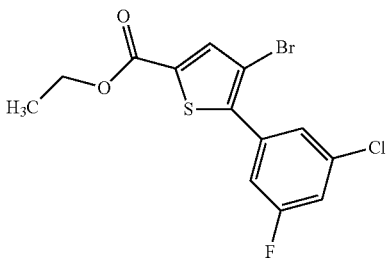 [SMILES: CCOC(=O)c1cc(Br)c(-c2cc(F)cc(Cl)c2)s1]

Under argon, 3.71 g (11.8 mmol) of the compound from Example 8A and 2.16 g (12.4 mmol) of 3-chloro-5-fluorophenylboronic acid are provided in 125 ml of degassed toluene/water (2.2/1), and 6.75 g (63.7 mmol) of sodium carbonate and 409 mg (0.35 mmol) of tetrakis(triphenylphosphine)palladium(0) are added. The mixture is stirred at 60° C. overnight. Water is added to the reaction mixture, the phases are separated, the aqueous phase is extracted with dichloromethane and the combined organic phases are dried over sodium sulfate, filtered and concentrated. The crude product is purified by preparative HPLC (RP18 column; eluent: acetonitrile/water gradient). This gives 1.17 g (27% of theory) of the title compound are obtained.

$^1$H-NMR (400 MHz, DMSO-$d_6$): δ=7.90 (s, 1H), 7.66-7.54 (m, 3H), 4.34 (q, 2H), 1.31 (t, 3H).

LC-MS (Method 1): $R_t$=3.22 min; MS (ESIpos): m/z=363 [M+H]$^+$.

Example 10A

Ethyl 4-bromo-5-(3-chlorophenyl)thiophene-2-carboxylate

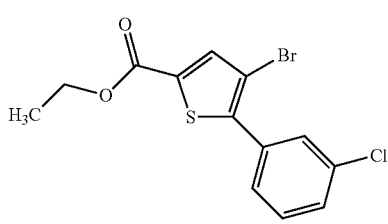 [SMILES: CCOC(=O)c1cc(Br)c(-c2cccc(Cl)c2)s1]

The preparation of the title compound takes place in analogy to the synthesis of the compound from Example 9A starting with the compound from Example 8A. 125 mg (57% of theory) of the title compound are obtained.

$^1$H-NMR (400 MHz, DMSO-$d_6$): δ=7.88 (s, 1H), 7.77-7.73 (m, 1H), 7.67-7.54 (m, 3H), 4.33 (q, 2H), 1.31 (t, 3H).

GC-MS (Method 11): $R_t$=7.91 min; MS (EIpos): m/z=346 [M]$^+$.

Example 11A

Ethyl 5-(3-chloro-5-fluorophenyl)-4-(3-cyanophenyl)thiophene-2-carboxylate

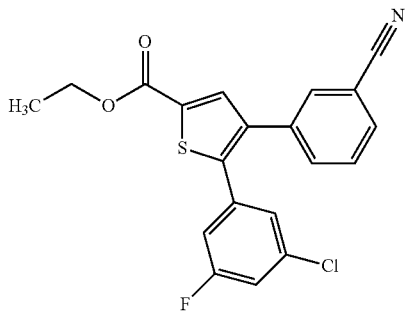 [SMILES: CCOC(=O)c1cc(-c2cccc(C#N)c2)c(-c2cc(F)cc(Cl)c2)s1]

Under argon, 400 mg (1.10 mmol) of the compound from Example 9A and 242 mg (1.65 mmol) of 3-cyanophenylboronic acid are provided in 15.7 ml of 1,2-dimethoxyethane, and 5.8 ml (5.50 mmol) of an aqueous sodium bicarbonate solution (10%) and 38.1 mg (0.03 mmol) of tetrakis(triphenylphosphine)palladium(0) are added. The mixture is stirred at 80° C. overnight. The reaction mixture is purified by preparative HPLC (RP18 column; eluent: acetonitrile/water gradient with addition of 0.1% formic acid). 130 mg (27% of theory) of the title compound are obtained.

GC-MS (Method 12): $R_t$=9.85 min; MS (EIpos): m/z=385 [M]$^+$.

Example 12A

Ethyl 4-(3-chloro-4-fluorophenyl)-5-(3-chloro-5-fluorophenyl)thiophene-2-carboxylate

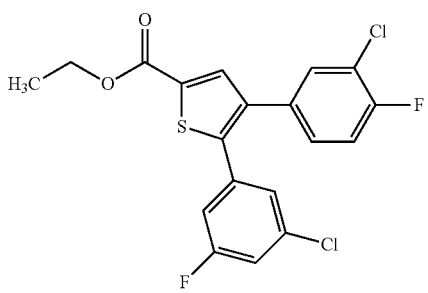 [SMILES: CCOC(=O)c1cc(-c2ccc(F)c(Cl)c2)c(-c2cc(F)cc(Cl)c2)s1]

The preparation of the title compound takes place in analogy to the synthesis of the compound from Example 11A starting with the compound from Example 9A. 59.8 mg (46% of theory) of the title compound are obtained.

$^1$H-NMR (400 MHz, DMSO-$d_6$): δ=7.96 (s, 1H), 7.61 (dd, 1H), 7.52 (dt, 1H), 7.41 (t, 1H), 7.26-7.16 (m, 3H), 4.34 (q, 2H), 1.32 (t, 3H).

LC-MS (Method 1): $R_t$=3.36 min; MS (ESIpos): m/z=317 [M+H]$^+$.

Example 13A

Ethyl 4-(3-chlorophenyl)thiophene-2-carboxylate

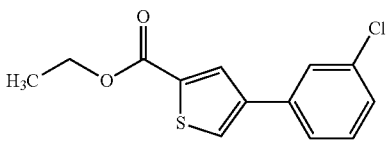 [SMILES: CCOC(=O)c1cc(-c2cccc(Cl)c2)cs1]

Under argon, 5.00 g (21.3 mmol) of the compound from Example 7A and 4.99 g (31.9 mmol) of 3-chlorophenylboronic acid are provided in 150 ml of 1,2-dimethoxyethane, and 113 ml (106 mmol) of an aqueous sodium bicarbonate solution (10%) and 737 mg (0.64 mmol) of tetrakis(triphenylphosphine)palladium(0) are added. The mixture is stirred at 80° C. for 1.5 hours. A 1N aqueous HCl solution is subsequently added, the mixture is extracted with ethyl acetate, the extract is concentrated and the residue is purified by flash chromatography (mobile phase: cyclohexane/ethyl acetate gradient). 5.60 g (88% of theory) of the title compound are obtained.

$^1$H-NMR (400 MHz, DMSO-$d_6$): δ=8.38 (d, 1H), 8.27 (d, 1H), 7.90 (t, 1H), 7.77 (dt, 1H), 7.46 (t, 1H), 7.41-7.37 (m, 1H), 4.33 (q, 2H), 1.32 (t, 3H).

LC-MS (Method 5): $R_t$=1.47 min; MS (ESIpos): m/z=267 [M+H]$^+$.

Example 14A

Ethyl 5-bromo-4-(3-chlorophenyl)thiophene-2-carboxylate

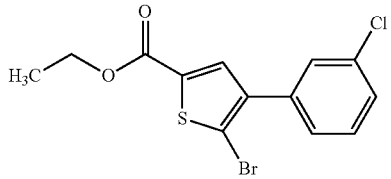 [SMILES: CCOC(=O)c1cc(-c2cccc(Cl)c2)c(Br)s1]

0.01 ml (0.22 mmol) of bromine is provided in 1 ml of acetic acid, and 58.0 mg (0.22 mmol) of the compound from Example 13A, dissolved in 1 ml of acetic acid, are added dropwise. The mixture is stirred at 60° C. overnight. 0.01 ml (0.22 mmol) of bromine is a subsequently added, and the mixture is stirred at 60° C. for another 24 hours. Water is added to the reaction mixture, and the resulting precipitate is collected by suction filtration, washed with water and dried under high vacuum. 43.0 mg (54% of theory) of the title compound are obtained.

$^1$H-NMR (400 MHz, DMSO-d$_6$): δ=7.88 (s, 1H), 7.68-7.66 (m, 1H), 7.59-7.54 (m, 1H), 7.54-7.51 (m, 2H), 4.32 (q, 2H), 1.30 (t, 3H).

LC-MS (Method 1): R$_t$=3.35 min; MS (ESIpos): m/z=345 [M+H]$^+$.

Example 15A

5-Bromo-4-(3-chlorophenyl)thiophene-2-carboxylic acid

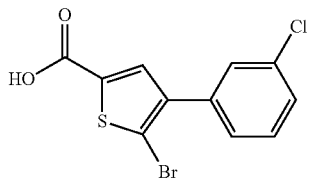 [SMILES: O=C(O)c1cc(-c2cccc(Cl)c2)c(Br)s1]

41.0 mg (0.12 mmol) of the compound from Example 14A are provided in 3 ml of tetrahydrofuran, and 28.4 mg (1.19 mmol) of lithium hydroxide and 0.8 ml of water are added at room temperature. The mixture is stirred at room temperature overnight, a 1N aqueous HCl solution is subsequently added until an acidic pH is obtained, the mixture is extracted three times with dichloromethane and the extracts are dried over sodium sulfate, filtered and concentrated. 35.0 mg (83% of theory) of the title compound are obtained.

$^1$H-NMR (400 MHz, DMSO-d$_6$): δ=13.6 (s, 1H), 7.77 (s, 1H), 7.66 (s, 1H), 7.58-7.54 (m, 1H), 7.53-7.50 (m, 2H).

LC-MS (Method 1): R$_t$=2.85 min; MS (ESIpos): m/z=317 [M+H]$^+$.

Example 16A

1-{[5-Bromo-4-(3-chlorophenyl)thiophen-2-yl]carbonyl}imidazolidin-4-one

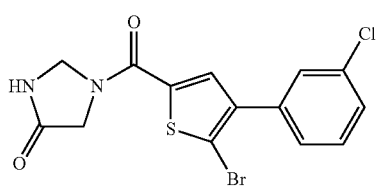 [SMILES: O=C1CN(C(=O)c2cc(-c3cccc(Cl)c3)c(Br)s2)CN1]

35.0 mg (0.11 mmol) of the compound from Example 15A, 10.4 mg (0.12 mmol) of 4-imidazolidinone and 86.0 mg (0.17 mmol) of PyBOP are provided in 2.8 ml of tetrahydrofuran, and 0.04 ml (0.23 mmol) of N,N-diisopropylethylamine are added at room temperature. The reaction mixture is stirred at room temperature overnight and then purified by preparative HPLC (RP18 column; eluent: acetonitrile/water gradient). 27.0 mg (62% of theory) of the title compound are obtained.

$^1$H-NMR (400 MHz, DMSO-d$_6$): δ=8.77 (s, 1H), 7.77 (s, 1H), 7.72 (s, 1H), 7.64-7.59 (m, 1H), 7.55-7.50 (m, 2H), 5.27 (s, 0.5H), 4.85 (s, 1.5H), 4.44 (s, 1.5H), 3.95 (s, 0.5H).

LC-MS (Method 7): R$_t$=1.80 min; MS (ESIpos): m/z=385 [M+H]$^+$.

Example 17A

Ethyl 5-(3-chlorophenyl)-4-(3-cyanophenyl)thiophene-2-carboxylate

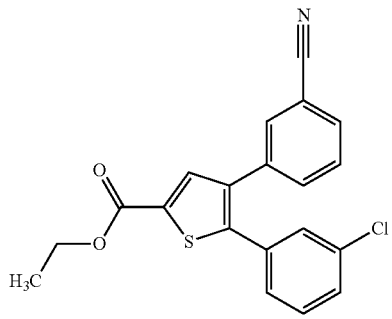 [SMILES: CCOC(=O)c1cc(-c2cccc(C#N)c2)c(-c2cccc(Cl)c2)s1]

Under argon, 3.20 g (9.26 mmol) of the compound from Example 10A are provided in 100 ml of 1,2-dimethoxyethane, and 1.36 g (9.26 mmol) of 3-cyanophenylboronic acid, 9.05 g (27.8 mmol) of cesium carbonate, 309 mg (0.65 mmol) of dicyclohexyl[2',4',6'-tri(propan-2-yl)biphenyl-2-yl]phosphane and 62.4 mg (0.28 mmol) of palladium(II) acetate are added. The mixture is stirred at 50° C. for three hours. The reaction mixture is subsequently diluted with water and extracted with dichloromethane, and the organic phase is dried over magnesium sulfate, filtered and concentrated. The crude product is purified by flash chromatography (mobile phase: cyclohexane/ethyl acetate gradient) on silica gel. 1.71 g (50% of theory) of the title compound are obtained.

$^1$H-NMR (400 MHz, DMSO-d$_6$): δ=8.00 (s, 1H), 7.87-7.84 (m, 1H), 7.83-7.78 (m, 1H), 7.57-7.51 (m, 2H), 7.51-7.47 (m, 1H), 7.42 (t, 1H), 7.38 (t, 1H), 7.25 (dt, 1H), 4.35 (q, 2H), 1.32 (t, 3H).

LC-MS (Method 1): R$_t$=3.23 min; MS (ESIpos): m/z=368 [M+H]$^+$.

Example 18A

Ethyl 5-(3-chloro-5-fluorophenyl)-4-(3-cyano-4-fluorophenyl)thiophene-2-carboxylate

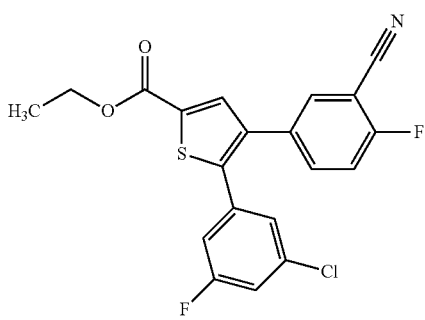 [SMILES: CCOC(=O)c1cc(-c2ccc(F)c(C#N)c2)c(-c2cc(F)cc(Cl)c2)s1]

Under argon, 220 mg (0.61 mmol) of the compound from Example 9A are provided in 6.2 ml of 1,2-dimethoxyethane, and 100 mg (0.61 mmol) of 3-cyano-4-fluorophenylboronic acid, 593 mg (1.82 mmol) of cesium carbonate, 20.0 mg (0.04 mmol) of dicyclohexyl[2',4',6'-tri(propan-2-yl)biphenyl-2-yl]phosphane and 4.0 mg (0.02 mmol) of palladium(II) acetate are added. The mixture is stirred at 50° C. overnight. The same amount of catalyst and ligand is added once more, and the mixture is stirred at 50° C. overnight. The reaction mixture is purified by preparative HPLC (RP18 column; eluent: acetonitrile/water gradient with addition of 0.1% formic acid). 86.0 mg (35% of theory) of the title compound are obtained.

$^1$H-NMR (400 MHz, DMSO-d$_6$): δ=8.04-8.00 (m, 2H), 7.61-7.47 (m, 3H), 7.27-7.24 (m, 1H), 7.19 (dt, 1H), 4.35 (q, 2H), 1.32 (t, 3H).

LC-MS (Method 1): R$_t$=3.12 min; MS (ESIpos): m/z=404 [M+H]$^+$.

Example 19A 5-(3-chloro-5-fluorophenyl)-4-(3-cyanophenyl)thiophene-2-carboxylic acid

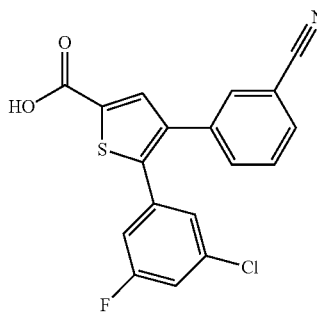

130 mg (0.34 mmol) of the compound from Example 11A are provided in 6.1 ml of tetrahydrofuran, and 80.7 mg (3.37 mmol) of lithium hydroxide and 2.0 ml of water are added at room temperature. The mixture is stirred at room temperature overnight, a 1N aqueous HCl solution is subsequently added until an acidic pH is obtained, the mixture is extracted with ethyl acetate and the extract is dried over sodium sulfate, filtered and concentrated. 119 mg (89% of theory) of the title compound are obtained.

$^1$H-NMR (400 MHz, DMSO-d$_6$): δ=13.5 (s, 1H), 7.93 (s, 1H), 7.87-7.84 (m, 1H), 7.84-7.80 (m, 1H), 7.57-7.49 (m, 3H), 7.23-7.20 (m, 1H), 7.16 (ddd, 1H).

LC-MS (Method 1): R$_t$=2.68 min; MS (ESIpos): m/z=358 [M+H]$^+$.

Example 20A 4-(3-Chloro-4-fluorophenyl)-5-(3-chloro-5-fluorophenyl)thiophene-2-carboxylic acid

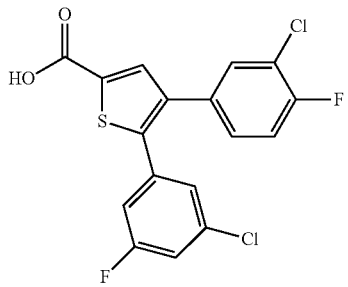 [SMILES: O=C(O)c1cc(-c2ccc(F)c(Cl)c2)c(-c2cc(F)cc(Cl)c2)s1]

The preparation of the title compound takes place in analogy to the synthesis of the compound from Example 19A starting with the compound from Example 12A. The organic phase is concentrated and purified by flash chromatography (mobile phase: cyclohexane/ethyl acetate/ethyl acetate:methanol 1:1 gradient) on silica gel. 0.43 g (100% of theory) of the title compound are obtained.

$^1$H-NMR (400 MHz, DMSO-d$_6$): δ=13.5 (s, 1H), 7.87 (s, 1H), 7.59 (dd, 1H), 7.51 (dt, 1H), 7.40 (t, 1H), 7.25-7.19 (m, 2H), 7.17 (dt, 1H).

LC-MS (Method 5): R$_t$=1.50 min; MS (ESIneg): m/z=385 [M−H]$^-$.

Example 21A 5-(3-Chlorophenyl)-4-(3-cyanophenyl)thiophene-2-carboxylic acid

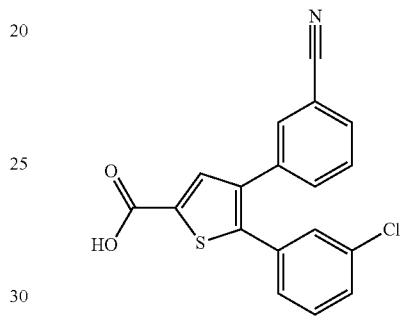

182 mg (0.50 mmol) of the compound from Example 17A are provided in 2 ml of dioxane, and 4.4 ml (8.80 mmol) of a 2N aqueous lithium hydroxide solution are added. The mixture is stirred at 50° C. for 2 hours and subsequently concentrated. The residue is diluted with water, a concentrated aqueous HCl solution is added until an acidic pH is obtained and the mixture is extracted with dichloromethane. The organic phase is dried over magnesium sulfate, filtered and concentrated. The crude product is purified by preparative HPLC (RP18 column; eluent: acetonitrile/water gradient). 159 mg (95% of theory) of the title compound are obtained.

$^1$H-NMR (400 MHz, DMSO-d$_6$): δ=13.5 (s, 1H), 7.91 (s, 1H), 7.84-7.77 (m, 2H), 7.57-7.51 (m, 2H), 7.50-7.45 (m, 1H), 7.41 (t, 1H), 7.36 (t, 1H), 7.24 (dt, 1H).

LC-MS (Method 9): R$_t$=2.31 min; MS (ESIneg): m/z=338 [M−H]$^-$.

Example 22A 5-(3-Chloro-5-fluorophenyl)-4-(3-cyano-4-fluorophenyl)thiophene-2-carboxylic acid

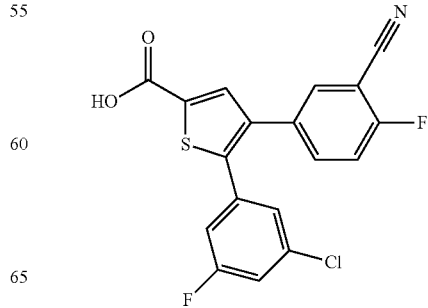

The preparation of the title compound takes place in analogy to the synthesis of the compound from Example 19A starting with the compound from Example 18A. 82.3 mg (97% of theory) of the title compound are obtained.

$^1$H-NMR (400 MHz, DMSO-$d_6$): δ=13.5 (br. s, 1H), 7.99 (dd, 1H), 7.93 (s, 1H), 7.58 (ddd, 1H), 7.55-7.47 (m, 2H), 7.24 (t, 1H), 7.17 (ddd, 1H).

LC-MS (Method 1): $R_t$=2.75 min; MS (ESIpos): m/z=376 [M+H]$^+$.

Example 23A

4-Bromo-5-(3-chlorophenyl)thiophene-2-carboxylic acid

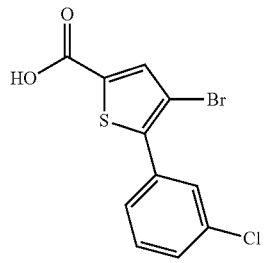 [SMILES: O=C(O)c1cc(Br)c(-c2cccc(Cl)c2)s1]

The preparation of the title compound takes place in analogy to the synthesis of the compound from Example 19A starting with the compound from Example 10A. 1.11 g (100% of theory) of the title compound are obtained.

$^1$H-NMR (400 MHz, DMSO-$d_6$): δ=13.7 (s, 1H), 7.78 (s, 1H), 7.75-7.72 (m, 1H), 7.63 (dt, 1H), 7.61-7.54 (m, 2H).

LC-MS (Method 7): $R_t$=2.13 min; MS (ESIneg): m/z=317 [M–H]$^-$.

Example 24A

1-{[4-Bromo-5-(3-chlorophenyl)thiophen-2-yl]carbonyl}imidazolidin-4-one

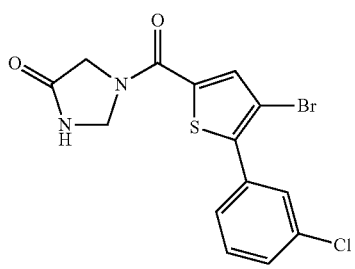 [SMILES: O=C1CN(C(=O)c2cc(Br)c(-c3cccc(Cl)c3)s2)CN1]

334 mg (1.05 mmol) of the compound from Example 23A, 332 mg (1.16 mmol) of 4-imidazolidinone and 821 mg (1.58 mmol) of PyBOP are provided in 7.2 ml of tetrahydrofuran, and 0.4 ml (2.21 mmol) of N,N-diisopropylethylamine are added at room temperature. The mixture is stirred at room temperature overnight, and the reaction mixture is subsequently purified by preparative HPLC (RP18 column; eluent: acetonitrile/water gradient). 226 mg (56% of theory) of the title compound are obtained.

$^1$H-NMR (400 MHz, DMSO-$d_6$): δ=8.78 (s, 1H), 7.83 (s, 1H), 7.74 (s, 1H), 7.67-7.52 (m, 3H), 5.24 (s, 0.5H), 4.87 (s, 1.5H), 4.41 (s, 1.5H), 3.97 (s, 0.5H).

LC-MS (Method 1): $R_t$=2.35 min; MS (ESIpos): m/z=387 [M+H]$^+$.

Exemplary Embodiments

Example 1

3-{2-(3-Chloro-5-fluorophenyl)-5-[(4-oxoimidazolidin-1-yl)carbonyl]thiophen-3-yl}benzenecarbonitrile

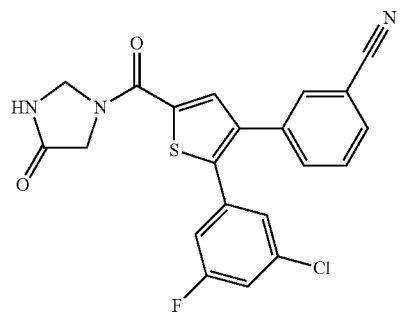 [SMILES: N#Cc1cccc(-c2cc(C(=O)N3CNC(=O)C3)sc2-c2cc(F)cc(Cl)c2)c1]

40.5 mg of the compound from Example 19A having a purity of 76% (0.08 mmol), 24.9 mg (0.13 mmol) of the compound from Example 4A and 88.4 mg (0.17 mmol) of PyBOP are provided in 2 ml of tetrahydrofuran, and 0.04 ml (0.24 mmol) of N,N-diisopropylethylamine are added at room temperature. The reaction mixture is stirred at room temperature overnight and subsequently purified by preparative HPLC (RP18 column; eluent: acetonitrile/water gradient with addition of 0.1% formic acid). 16.8 mg (46% of theory) of the title compound are obtained.

$^1$H-NMR (400 MHz, DMSO-$d_6$): δ=8.85-8.76 (m, 1H), 7.98 (s, 1H), 7.90 (s, 1H), 7.84-7.80 (m, 1H), 7.55-7.49 (m, 3H), 7.22-7.20 (m, 1H), 7.15 (ddd, 1H), 5.31 (s, 0.5H), 4.89 (s, 1.5H), 4.48 (s, 1.5H), 3.99 (s, 0.5H).

LC-MS (Method 1): $R_t$=2.37 min; MS (ESIpos): m/z=426 [M+H]$^+$.

Example 2

1-{[4-(3-Chloro-4-fluorophenyl)-5-(3-chloro-5-fluorophenyl)thiophen-2-yl]carbonyl}imidazolidin-4-one

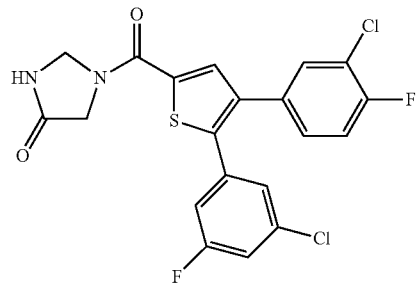 [SMILES: O=C1CN(C(=O)c2cc(-c3ccc(F)c(Cl)c3)c(-c3cc(F)cc(Cl)c3)s2)CN1]

The preparation of the title compound takes place in analogy to the synthesis of the compound from Example 1 starting with 49.1 mg (0.13 mmol) of the compound from Example 20A. 40.9 mg (71% of theory) of the title compound are obtained.

33

$^1$H-NMR (400 MHz, DMSO-d$_6$): δ=8.85-8.75 (m, 1H), 7.86 (s, 0.75H), 7.75 (s, 0.25H), 7.72-7.65 (m, 1H), 7.50 (dt, 1H), 7.40 (t, 1H), 7.25-7.19 (m, 2H), 7.16 (dt, 1H), 5.30 (s, 0.5H), 4.89 (s, 1.5H), 4.47 (s, 1.5H), 3.98 (s, 0.5H).

LC-MS (Method 1): R$_t$=2.58 min; MS (ESIpos): m/z=453 [M+H]$^+$.

Example 3

3-{2-(3-Chlorophenyl)-5-[(4-oxoimidazolidin-1-yl)carbonyl]thiophen-3-yl}benzenecarbonitrile

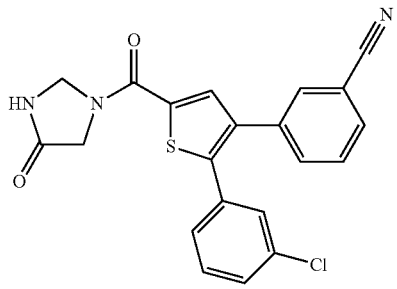 [SMILES: N#Cc1cccc(-c2cc(C(=O)N3CNC(=O)C3)sc2-c2cccc(Cl)c2)c1]

31.3 mg (0.09 mmol) of the compound from Example 21A, 9.5 mg (0.11 mmol) of 4-imidazolidinone and 52.7 mg (0.10 mmol) of PyBOP are provided in 0.7 ml of tetrahydrofuran, and 0.02 ml (0.10 mmol) of N,N-diisopropylethylamine are added at room temperature. The reaction mixture is stirred at room temperature overnight and subsequently purified by preparative HPLC (RP18 column; eluent: acetonitrile/water gradient). 15.9 mg (42% of theory) of the title compound are obtained.

$^1$H-NMR (400 MHz, DMSO-d$_6$): δ=8.85-8.75 (m, 1H), 7.97-7.87 (m, 2H), 7.83-7.78 (m, 1H), 7.54-7.50 (m, 2H), 7.47 (d, 1H), 7.41 (t, 1H), 7.36 (s, 1H), 7.24 (d, 1H), 5.31 (s, 0.5H), 4.89 (s, 1.5H), 4.48 (s, 1.5H), 3.99 (s, 0.5H).

LC-MS (Method 1): R$_t$=2.40 min; MS (ESIpos): m/z=408 [M+H]$^+$.

Example 4

5-{2-(3-Chloro-5-fluorophenyl)-5-[(4-oxoimidazolidin-1-yl)carbonyl]thiophen-3-yl}-2-fluorobenzenecarbonitrile

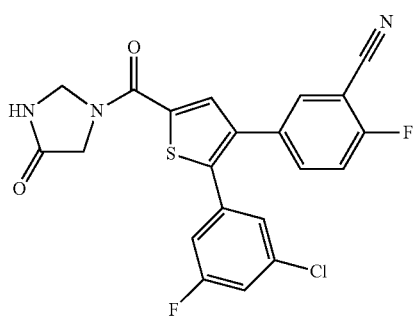 [SMILES: N#Cc1cc(-c2cc(C(=O)N3CNC(=O)C3)sc2-c2cc(F)cc(Cl)c2)ccc1F]

The preparation of the title compound takes place in analogy to the synthesis of the compound from Example 1 starting with 82.3 mg (0.22 mmol) of the compound from Example 22A. 35.0 mg (35% of theory) of the title compound are obtained.

34

$^1$H-NMR (400 MHz, DMSO-d$_6$): δ=8.87-8.76 (m, 1H), 8.13-8.07 (m, 1H), 7.91-7.75 (m, 1H), 7.60-7.47 (m, 3H), 7.25 (s, 1H), 7.17 (d, 1H), 5.30 (s, 0.5H), 4.89 (s, 1.5H), 4.47 (s, 1.5H), 3.98 (s, 0.5H).

LC-MS (Method 1): R$_t$=2.39 min; MS (ESIpos): m/z=444 [M+H]$^+$.

Example 5

1-{[5-(3-Chloro-5-fluorophenyl)-4-(3-chlorophenyl)thiophen-2-yl]carbonyl}imidazolidin-4-one

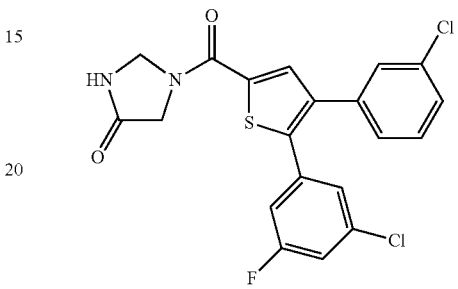

Under argon, 49.0 mg (0.13 mmol) of the compound from Example 16A and 33.2 mg (0.19 mmol) of 3-chloro-5-fluorophenylboronic acid are provided in 1.8 ml of 1,2-dimethoxyethane, and 0.7 ml (0.64 mmol) of an aqueous sodium bicarbonate solution (10%) and 4.4 mg (0.004 mmol) of tetrakis(triphenylphosphine)palladium(0) are added. The mixture is stirred at 80° C. overnight. The reaction mixture is purified by preparative HPLC (RP18 column; eluent: acetonitrile/water gradient with addition of 0.1% formic acid). 12.0 mg (22% of theory) of the title compound are obtained.

$^1$H-NMR (400 MHz, DMSO-d$_6$): δ=8.78 (s, 1H), 7.88-7.70 (m, 1H), 7.53-7.47 (m, 2H), 7.43 (dt, 1H), 7.38 (t, 1H), 7.22-7.18 (m, 2H), 7.14 (dt, 1H), 5.31 (s, 0.5H), 4.89 (s, 1.5H), 4.48 (s, 1.5H), 3.99 (s, 0.5H).

LC-MS (Method 7): R$_t$=2.13 min; MS (ESIpos): m/z=435 [M+H]$^+$.

Example 6

5-{3-(3-Chlorophenyl)-5-[(4-oxoimidazolidin-1-yl)carbonyl]thiophen-2-yl}-2-fluorobenzenecarbonitrile

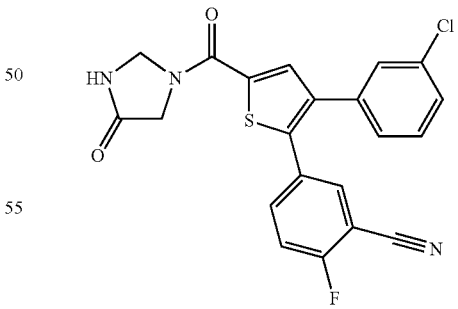

Under argon, 70.0 mg (0.15 mmol) of the compound from Example 16A and 36.1 mg (0.22 mmol) of 3-cyano-4-fluorophenylboronic acid were provided in 2.1 ml of 1,2-dimethoxyethane, and 0.8 ml (0.73 mmol) of an aqueous sodium bicarbonate solution (10%) and 5.1 mg (0.004 mmol) of tetrakis(triphenylphosphine)palladium(0) are added. The mixture is stirred at 80° C. overnight. The reaction mixture is purified by preparative HPLC (RP18 column; eluent: acetonitrile/water gradient with addition of 0.1% formic acid) and additional preparative thin-layer chromatography (silica gel; mobile phase: dichloromethane/methanol 10/1). 5.3 mg (9% of theory) of the title compound are obtained.

$^1$H-NMR (400 MHz, DMSO-d$_6$): δ=8.78 (s, 1H), 7.87-7.71 (m, 1H), 7.53-7.47 (m, 1H), 7.43 (dt, 1H), 7.38 (t, 1H), 7.31 (tt, 1H), 7.20 (d, 1H), 7.06-6.99 (m, 2H), 5.31 (s, 0.5H), 4.89 (s, 1.5H), 4.48 (s, 1.5H), 3.99 (s, 0.5H).

LC-MS (Method 7): R$_t$=1.88 min; MS (ESIpos): m/z=426 [M+H]$^+$.

Example 7

1-({4-(3-Chlorophenyl)-5-[3-(trifluoromethoxy)phenyl]thiophen-2-yl}carbonyl)imidazolidin-4-one

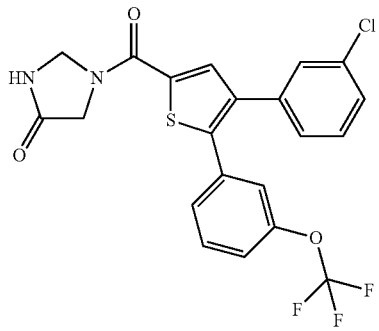 [SMILES: O=C1CN(C(=O)c2cc(-c3cccc(Cl)c3)c(-c3cccc(OC(F)(F)F)c3)s2)CN1]

The preparation of the title compound takes place in analogy to the synthesis of the compound from Example 5 starting with 70.0 mg (0.15 mmol) of the compound from Example 16A and 45.1 mg (0.22 mmol) of 3-(trifluoromethoxy)phenylboronic acid. 26.7 mg (39% of theory) of the title compound are obtained.

$^1$H-NMR (400 MHz, DMSO-d$_6$): δ=8.78 (s, 1H), 7.86 (s, 0.75H), 7.74 (s, 0.25H), 7.56 (t, 1H), 7.46-7.33 (m, 5H), 7.21 (d, 1H), 7.14 (s, 1H), 5.31 (s, 0.5H), 4.89 (s, 1.5H), 4.48 (s, 1.5H), 3.99 (s, 0.5H).

LC-MS (Method 7): R$_t$=2.17 min; MS (ESIpos): m/z=467 [M+H]$^+$.

Example 8

5-{2-(3-Chlorophenyl)-5-[(4-oxoimidazolidin-1-yl)carbonyl]thiophen-3-yl}-2-fluorobenzenecarbonitrile

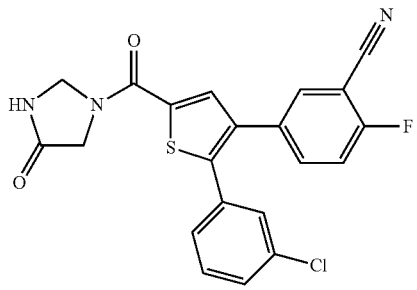 [SMILES: N#Cc1cc(-c2cc(C(=O)N3CNC(=O)C3)sc2-c2cccc(Cl)c2)ccc1F]

Under argon, 61.0 mg (0.16 mmol) of the compound from Example 24A are provided in 3 ml of 1,2-dimethoxyethane, and 26.1 mg (0.16 mmol) of 3-cyano-4-fluorophenylboronic acid, 155 mg (0.47 mmol) of cesium carbonate, 5.3 mg (0.01 mmol) of dicyclohexyl[2',4',6'-tri(propan-2-yl)biphenyl-2-yl]phosphane and 1.1 mg (0.005 mmol) of palladium(II) acetate are added. The mixture is heated in a closed glass vessel at 100° C. under microwave irradiation for 30 minutes. The reaction mixture is purified by preparative HPLC (RP18 column; eluent: acetonitrile/water gradient). 23.0 mg (34% of theory) of the title compound are obtained.

$^1$H-NMR (400 MHz, DMSO-d$_6$): δ=8.86-8.74 (m, 1H), 8.09-8.02 (m, 1H), 7.90-7.73 (m, 1H), 7.56 (ddd, 1H), 7.52-7.46 (m, 2H), 7.44-7.38 (m, 2H), 7.23 (d, 1H), 5.31 (s, 0.5H), 4.89 (s, 1.5H), 4.48 (s, 1.5H), 3.99 (s, 0.5H).

LC-MS (Method 1): R$_t$=2.50 min; MS (ESIpos): m/z=426 [M+H]$^+$.

Example 9

1-{[4-(3-Chloro-4-fluorophenyl)-5-(3-chlorophenyl)thiophen-2-yl]carbonyl}imidazolidin-4-one

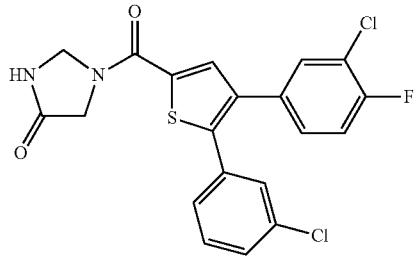 [SMILES: O=C1CN(C(=O)c2cc(-c3ccc(F)c(Cl)c3)c(-c3cccc(Cl)c3)s2)CN1]

Under argon, 70.0 mg of the compound from Example 24A having a purity of 76% (0.14 mmol) and 47.5 mg (0.27 mmol) of 3-chloro-4-fluorophenylboronic acid are provided in 2.6 ml of 1,2-dimethoxyethane, and 1.0 ml (0.91 mmol) of an aqueous sodium bicarbonate solution (10%) and 6.3 mg (0.005 mmol) of tetrakis(triphenylphosphine)palladium(0) are added. The mixture is heated in a closed glass vessel at 150° C. under microwave irradiation for 5 minutes. The reaction mixture is purified by preparative HPLC (RP18 column; eluent: acetonitrile/water gradient with addition of 0.1% formic acid) and additional preparative thin-layer chromatography (silica gel; mobile phase: ethyl acetate). 8.0 mg (13% of theory) of the title compound are obtained.

$^1$H-NMR (400 MHz, DMSO-d$_6$): δ=8.82-8.75 (m, 1H), 7.87-7.71 (m, 1H), 7.69-7.63 (m, 1H), 7.49-7.35 (m, 4H), 7.27-7.18 (m, 2H), 5.30 (s, 0.5H), 4.88 (s, 1.5H), 4.47 (s, 1.5H), 3.98 (s, 0.5H).

LC-MS (Method 1): R$_t$=2.54 min; MS (ESIpos): m/z=435 [M+H]$^+$.

Example 10

3-{3-(3-Chloro-4-fluorophenyl)-5-[(4-oxoimidazolidin-1-yl)carbonyl]thiophen-2-yl}-5-fluorobenzenecarbonitrile

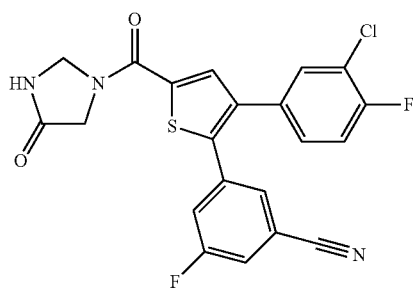 [SMILES: N#Cc1cc(F)cc(-c2sc(C(=O)N3CNC(=O)C3)cc2-c2ccc(F)c(Cl)c2)c1]

Under argon, 1.50 g (4.78 mmol) of the compound from Example 8A are provided in 75 ml of 1,2-dimethoxyethane, and 1.30 g (5.26 mmol) of the compound from Example 5A, 4.67 g (14.3 mmol) of cesium carbonate, 159 mg (0.33 mmol) of dicyclohexyl[2',4',6'-tri(propan-2-yl)biphenyl-2-yl]phosphane and 32.0 mg (0.14 mmol) of palladium(II) acetate are added. The mixture is stirred at 50° C. overnight. Water is subsequently added, the mixture is extracted with ethyl acetate and the extract is dried over sodium sulfate, filtered and concentrated. The crude product is purified by preparative HPLC (RP18 column; eluent: acetonitrile/water gradient with addition of 0.1% formic acid). 1.05 g of ethyl 4-bromo-5-(3-cyano-5-fluorophenyl)thiophene-2-carboxylate are obtained.

LC-MS (Method 1): $R_t$=2.91 min; MS (ESIpos): m/z=354 $[M+H]^+$.

Under argon, half of the solid obtained in this manner and 517 mg (2.96 mmol) of 3-chloro-4-fluorophenylboronic acid are provided in 21 ml of 1,2-dimethoxyethane, and 7.9 ml (7.41 mmol) of an aqueous sodium bicarbonate solution (10%) and 51.0 mg (0.04 mmol) of tetrakis(triphenylphosphine)palladium(0) are added. The mixture is stirred at 80° C. overnight. The mixture is subsequently concentrated, a 1N aqueous HCl solution is added until an acidic pH is obtained, the mixture is extracted with ethyl acetate and the extract is dried over sodium sulfate, filtered and concentrated. The crude product is purified by preparative HPLC (RP18 column; eluent: acetonitrile/water gradient with addition of 0.1% formic acid). 41.7 mg of ethyl 4-(3-chloro-4-fluorophenyl)-5-(3-cyano-5-fluorophenyl)thiophene-2-carboxylate are obtained.

GC-MS (Method 11): $R_t$=9.26 min; MS (EIpos): m/z=403 $[M]^+$.

The solid obtained in this manner is provided in 1.8 ml of tetrahydrofuran, and 24.7 mg (1.03 mmol) of lithium hydroxide and 0.6 ml of water are added at room temperature. The mixture is stirred at room temperature overnight, a 1N aqueous HCl solution is subsequently added until an acidic pH is obtained, and the mixture is extracted with ethyl acetate and the extract is dried over sodium sulfate, filtered and concentrated. 29.8 mg of 4-(3-chloro-4-fluorophenyl)-5-(3-cyano-5-fluorophenyl)thiophene-2-carboxylic acid are obtained. This solid, 16.0 mg (0.08 mmol) of the compound from Example 4A and 56.8 mg (0.11 mmol) of PyBOP are provided in 2 ml of tetrahydrofuran, and 0.04 ml (0.23 mmol) of N,N-diisopropylethylamine are added at room temperature. The reaction mixture is stirred at room temperature overnight and then purified by preparative HPLC (RP18 column; eluent: acetonitrile/water gradient with addition of 0.1% formic acid). 7.4 mg (1% of theory) of the title compound are obtained.

$^1$H-NMR (400 MHz, DMSO-$d_6$): δ=8.85-8.76 (m, 1H), 7.91 (ddd, 1H), 7.88 (s, 0.75H), 7.76 (s, 0.25H), 7.74-7.67 (m, 2H), 7.54 (dt, 1H), 7.39 (t, 1H), 7.19 (ddd, 1H), 5.31 (s, 0.5H), 4.89 (s, 1.5H), 4.48 (s, 1.5H), 3.99 (s, 0.5H).

LC-MS (Method 5): $R_t$=1.21 min; MS (ESIpos): m/z=444 $[M+H]^+$.

Example 11

3-{3-(3-Chlorophenyl)-5-[(4-oxoimidazolidin-1-yl)carbonyl]thiophen-2-yl}-5-fluorobenzenecarbonitrile

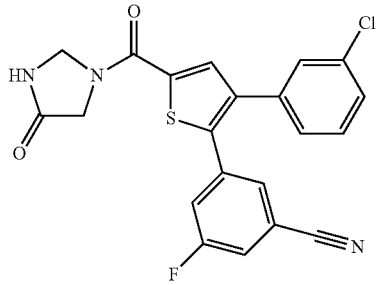 [SMILES: N#Cc1cc(F)cc(-c2sc(C(=O)N3CNC(=O)C3)cc2-c2cccc(Cl)c2)c1]

The preparation of the title compound takes place in analogy to the synthesis of the compound from Example 10 starting with the compound from Example 8A. 8.2 mg (1% of theory) of the title compound are obtained.

$^1$H-NMR (400 MHz, DMSO-$d_6$): δ=8.83-8.76 (m, 1H), 7.90 (ddd, 1H), 7.89-7.74 (m, 1H), 7.66 (s, 1H), 7.55-7.49 (m, 2H), 7.43 (ddd, 1H), 7.36 (t, 1H), 7.17 (d, 1H), 5.31 (s, 0.5H), 4.89 (s, 1.5H), 4.48 (s, 1.5H), 3.99 (s, 0.5H).

LC-MS (Method 5): $R_t$=1.20 min; MS (ESIpos): m/z=426 $[M+H]^+$.

B) Assessment of the Physiological Activity

Abbreviations:

| | |
|---|---|
| DMSO | dimethyl sulfoxide |
| FCS | fetal calf serum (Biochrom AG, Berlin, Germany) |
| PBS | phosphate buffered saline |
| MTP | microtiter plate |
| ELISA | enzyme-linked immunosorbent assay |

The suitability of the compounds of the invention for the treatment of diseases caused by retroviruses can be shown in the following assay systems:

In Vitro Assays

Biochemical Reverse Transcriptase Assay

The "Reverse Transcriptase Assay, colorimetric" (Roche Diagnostics GmbH, Mannheim, Germany) is used in accordance with the manufacturer's information. The test substances are dissolved in DMSO and are used in the test diluted in 5-fold steps (final DMSO concentration 1%). The resulting values of the photometric evaluation (405/492 nm) are less than 0.1 for the negative control (mixture without reverse transcriptase) and are in the region of 1.5 for the positive control (mixture without test substance). The $IC_{50}$ values of the test substances are determined as the concentration of the test substance dilution at which the measured optical density is 50% of the positive control.

It is found that the compounds of the invention inhibit the reverse transcriptase activity. Experimental data are summarized in Table A.

Light Assay with Wild-Type and Inhibitor-Resistant HI Reporter Viruses

HIV-1$_{NL4-3}$ reporter viruses which carry the lu164 gene (luciferase 164) instead of the nef gene are used for this assay. The viruses are generated by transfection of 293T cells with the corresponding proviral pNL4-3 plasmid (Lipofectamine Reagent, Invitrogen, Karlsruhe, Germany). Starting from the proviral plasmid DNA using the "QuikChange II XL Site-Directed Mutagenesis Kit" (Stratagene, Cedar Creek, Tex., USA) viruses with defined resistance mutations in the reverse transcriptase gene are produced. The following mutations, inter alia, are generated: A98G, A98G-K103N-V1081, A98S, F227C, F227L, G190A, G1905, K101E, K101Q-K103N, K103N, K103N-F227L, K103N-G190A, K103N-G1905, K103N-M230L, K103N-N3481, K103N-P225H, K103N-V1081, K103N-V1081-P225H, K103N-V179F-Y181C, K103N-Y181C, K103N-Y181C-G190A, L100I, L100I-K103N, L100I-K103N-V1791-Y181C, L100I-K103N-Y181C, L234I, N348I, P225H, P236L, V106A, V106A-E138K, V106A-F227C, V106A-F227L, V106I, V106I-Y188L, V106M, V108I, V179F-Y181C, V179I, V179I-

Y181C, Y181C, Y181C-G190A, Y181C-M230L, Y181I, Y188L. MT4 7F2 cells infected with these reporter viruses secrete luciferase into the medium, thus enabling virus replication to be quantified by luminometry.

For the mixture for a 96-well MTP, 3 million MT4 7F2 cells are pelleted, suspended in 1 ml of RPMI 1640 medium without phenol red (Invitrogen, Karlsruhe, Germany)/10% FCS/ 10% AIM-V (Invitrogen, Karlsruhe, Germany) and incubated together with a suitable amount of the corresponding HIV-$1_{NL4-3}$ reporter virus at 37° C. for 2 hours (pellet infection). Unadsorbed viruses are subsequently washed out with PBS, and the infected cells are pelleted again and suspended in 8 ml of RPMI 1640 medium without phenol red/2% or 10% FCS/ 10% AIM-V. 80 µl thereof are pipetted into each well of a white 96-well MTP with 20 µl of test substance in suitable dilution. To avoid edge effects, the wells on the edge of the MTP are not used for substance dilutions. The second vertical row of the MTP contains only infected cells (virus control) and the eleventh vertical row only uninfected cells (cell control), in each case in RPMI 1640 medium without phenol red/2% or 10% FCS/10% AIM-V. The other wells of the MTP contain the compounds of the invention in various concentrations starting from the third vertical row, from which the test substances are diluted in 3-fold steps up to the tenth vertical row $3^7$-fold. The test substances are dissolved in DMSO, whereby the final DMSO concentration in the test mixture is 1%. The test mixtures are incubated at 37° C./5% $CO_2$ for five days and, after the addition of 15 µl of Lu164 substrate (5 mg/ml coelenterazine dissolved in 30 µM glutathione/ DMSO, 100 mM NaCl, 1M MES, 100 mM glutathione), evaluated by luminometry. The resulting values are in the region of 1 000 000 RLUs (relative light units) for the virus control and 300 to 400 RLUs for the cell control. The $EC_{50}$ values of the test substances are determined as the concentration at which the virus replication measured in RLUs is 50% of the untreated infected cells.

It is found that the compounds of the invention inhibit the HIV replication. Experimental data are summarized in Table A.

PBL and H9 Assay with Wild-Type HIV-1

Primary human blood lymphocytes (PBLs) are isolated from blood using Ficoll-Paque Leucosep tubes (Greiner Bio-One, Frickenhausen, Germany) and stimulated with phytohaemagglutinin (90 µg/ml) and interleukin-2 (40 U/ml) in RPMI 1640 medium (Invitrogen, Karlsruhe, Germany)/10% FCS for 3 days.

For the mixture for a 96-well MTP, 3 million PBLs are pelleted, suspended in 1 ml of RPMI 1640 medium/10% FCS and incubated together with a suitable amount of HIV-$1_{LAI}$ (NIH AIDS Research & Reference Reagent Program, Germantown, USA) at 37° C. for 2 hours (pellet infection). Unadsorbed viruses are subsequently washed out with PBS, and the infected cells are pelleted again and suspended in 18 ml of RPMI 1640 medium/10% FCS/interleukin-2 (40 U/ml). 180 µl thereof are pipetted into each well of a white 96-well MTP with 20 µl of test substance in suitable dilution. Alternatively, after preparation of the substance dilutions in the MTP, the HIV is pipetted in together with the cells and is not washed out again (supernatant infection). In order to avoid edge effects, the wells at the edge of the MTP are not used for substance dilutions. The second vertical row of the MTP contains only infected cells (virus control) and the eleventh vertical row only uninfected cells (cell control), in each case in RPMI 1640 medium/10% FCS/interleukin-2 (40 U/ml). The other wells of the MTP contain the compounds of the invention in various concentrations starting from the third vertical row, from which the test substances are diluted in 3-fold steps up to the tenth vertical row $3^7$-fold. The test substances are dissolved in DMSO, whereby the final DMSO concentration in the test mixture is 1%. The test mixtures are incubated at 37° C./5% $CO_2$. After 5 and 7 days, 50 µl of cell-free supernatant are removed from each well to determine the amount of p24 present by means of a p24 ELISA (HIV-1 p24$^{CA}$ Antigen Capture Assay Kit, NCI-Frederick Cancer Research and Development Center, Frederick, USA). From the resulting values of the photometric evaluation (450/ 620 nm) the $EC_{50}$ values of the test substances are determined as the concentration at which the amount of p24 is 50% of the untreated infected cells.

Alternatively, H9 cells (ATCC, Wesel, Germany) are employed instead of PBLs for testing the test substances. H9 cells are incubated in RPMI 1640 medium with 2% or 10% FCS as a HIV-$1_{LAI}$ supernatant infection at 37° C./5% $CO_2$, (20 µl of substance dilution and 80 µl of cells/virus per well) in accordance with the pattern described above for 5 days. Subsequently, 10 µl of AlamarBlue (Invitrogen, Karlsruhe, Germany) are added to each well, and the MTPs are incubated at 37° C. for 3 hours before the fluorimetric evaluation takes place (544/590 nm). The resulting values are about 40 000 for the untreated uninfected cells and about 7000 for the untreated infected cells. In the low concentration range, the $EC_{50}$ values of the test substances are determined as the concentration at which the fluorescence is 50% of the untreated uninfected cells (in each case subtracting the values of the untreated infected cells). In addition, in the high concentration range, the $CC_{50}$ values of the test substances are determined as the concentration at which the fluorescence is 50% of the untreated uninfected cells (in each case subtracting the values of the untreated infected cells).

It is found that the compounds of the invention inhibit the HIV replication. Experimental data are summarized in Table A.

Assay to Determine the Cytotoxic Effect of the Test Substances

To determine the cytotoxic effect of the test substances in uninfected cells, the substances are pipetted in appropriate concentrations into transparent 96-well MTPs and incubated with uninfected cells (e.g., H9, PBLs, THP-1, MT4 7F2, CEM, Jurkat) (in analogy to the assays described above). After 5 days, per each well 1/10 of the volume AlamarBlue is added to the test mixtures, and the MTPs are incubated at 37° C. for 3 hours. The fluorimetric evaluation (544/590 nm) subsequently takes place. The resulting values are between 20 000 and 40 000 for untreated cells, depending on the type of cell. The $CC_{50}$ values of the test substances are determined as the concentration at which the fluorescence is 50% of the untreated cells. Test substances which show cytotoxic findings in the concentration range of the effect are not evaluated for their antiviral activity.

TABLE A

| Example No. | $IC_{50}$(nM) RT assay | $EC_{50}$(nM) H9 cells HIV-$1_{LAI}$ 10% FCS | $EC_{50}$(nM) MT4 7F2 cells HIV-$1_{NL4-3}$ wt 2% FCS | $EC_{50}$(nM) MT4 7F2 cells HIV-$1_{NL4-3}$ K103N-Y181C 2% FCS |
|---|---|---|---|---|
| Example 1 |  | 9 | 1 | 45 |
| Example 2 | 920 | 68 | 20 | 176 |
| Example 3 | 740 | 71 | 5 | 100 |
| Example 4 |  | 12 | <1.5 | 44 |
| Example 5 | 2170 | 85 | 21 | 258 |
| Example 6 |  | 900 | 165 | 348 |
| Example 7 |  | 1410 | 100 | 150 |
| Example 8 |  | 103 | 5 | 121 |
| Example 9 |  | 593 | 35 | 260 |

TABLE A-continued

| Example No. | IC$_{50}$(nM) RT assay | EC$_{50}$(nM) H9 cells HIV-1$_{LAI}$ 10% FCS | EC$_{50}$(nM) MT4 7F2 cells HIV-1$_{NL4-3}$ wt 2% FCS | EC$_{50}$(nM) MT4 7F2 cells HIV-1$_{NL4-3}$ K103N-Y181C 2% FCS |
|---|---|---|---|---|
| Example 10 | | 34 | 5 | 40 |
| Example 11 | | 22 | 2 | 123 |

In Vivo Assay

Animal Model:

NOD Scid mice, usually 5-6 weeks old, are purchased from commercial breeders (e.g., Taconic or Jackson Laboratory). The animals are kept under sterile conditions (including bedding and feed) in isolators.

A defined number of cells (e.g., $5\times10^6$ T cells (e.g., C8166)) is infected with HIV with a suitable m.o.i. (e.g., 0.01 TCID$^{50}$). The infected cells are introduced into collagen sponges. The sponges pretreated in this way are implanted under the dorsal skin of the mice. The mice are treated once or several times each day orally, intraperitoneally, subcutaneously or intravenously, whereby it is possible that the first treatment takes place before the implantation. The treatment groups usually include 10 mice. At least one group is treated with placebo, at least one group with a substance known to be active (=positive control) and usually several groups with the substance of the invention. The daily dose of the substance of the invention is between 0.01 mg and 100 mg per kg of body weight. The substances are formulated in 2% DMSO/0.5% methylcellulose in PBS or another suitable mixture which assists the solubility of the substances. The treatment usually lasts four and a half days. After the last administration of the substance, the animals are sacrificed and the sponges are removed. The virus-infected cells are obtained from the sponge by collagenase digestion.

The total RNA is obtained from the cells and is examined by quantitative PCR for the content of viral RNA. The amount of viral RNA is normalized on the basis of the amount of a housekeeping gene (e.g., GAPDH). The amount of HIV RNA after treatment with the substance compared with the placebo-treated control group is determined. If an HIV carrying a luciferase was used it is possible in addition or as substitute to carry out a luciferase measurement. In this case, the amount of HIV is determined from the level of the luciferase signal because it serves as a measure of the viral replication in this case. Statistical analysis takes place by means of suitable computer programs, e.g., Graph Pad Prism.

B) Assessment of the Pharmacokinetic Properties

In Vivo Studies

To determine the in vivo pharmacokinetics, the test substances are administered intravenously and orally to mice, rats and dogs. The dose chosen in intravenous studies for determining the pharmacokinetic properties of the test substances is 0.5 mg/kg in all species. On oral administration, 3 mg/kg is administered to the rodents, and 1 mg/kg to dogs. The test substances are formulated in 99% plasma, 1% DMSO for the intravenous administration for rodents, and in PEG 400, ethanol and water in varying proportions for oral administration. The latter vehicle is used for both administration routes for dogs.

Male Wistar rats are catheterized before the administration of the test substances so that the blood samples can be taken with the aid of the catheter in place or by puncture of the vena cava at various times over an interval of from 2 min up to 26 h.

The test substances are administered to female BalbC mice intravenously as bolus injection, and in this case samples are obtained exclusively by puncture of the vena cava over an interval of from 2 min up to 26 h. Administration to female beagle dogs exclusively takes place by a 15-minute intravenous infusion. The samples are obtained by puncture of the brachial vein or the jugular vein over an interval of from 10 min up to 26 h.

The substances are quantitatively determined from the animal plasma obtained and calibration samples adjusted in plasma. The plasma proteins are removed by precipitation with acetonitrile (ACN). The samples are subsequently fractionated by HPLC on an Agilent™ 1100 LC system (Agilent, Santa Clara, Calif., USA) using various columns, e.g., Luna C8, LichroCart Purospher Star RP18e. The HPLC system is coupled via a Turbo Ion Spray interface to an API 3000 triple quadropole mass spectrometer (Applied Biosystems, Darmstadt, Germany). The evaluation of the plasma concentration-time course takes place by employing an internal standard and using a validated kinetic analysis program.

Besides studies to determine the pharmacokinetic parameters of the test substances in vivo, determinations of the relative bioavailability from suspension (formulation: Tylose suspension) versus solution in the rat as well as high-dose studies preliminary to tests of effect and toxicological studies in mice, rats and dogs are carried out.

Plasma Stability

The plasma used from the various species (BalbC mouse, Wistar rat, beagle dog and human) is obtained fresh by taking blood into monovettes coated with Li-heparin and subsequent centrifugation. In order to determine the plasma stability of the test substances 2 ml containing in each case 500 ng/ml in plasma are incubated at 37° C. Samples are taken from the incubation vessel at various times over an interval of up to 3 h. The samples obtained are precipitated with ACN in order to stop the reaction and remove the plasma proteins. The samples are analyzed in a manner equivalent to the in vivo studies.

Microsomal and Hepatocyte Incubations

Incubations with liver microsomes of various species (BalbC mouse, Wistar rat, beagle dog, human) are carried out in a total volume of 1.5 ml at 37° C. in a modified Multiprobe II® robot system (Canberra Packard) or Janus® robot system (Perkin Elmer).

The incubation mixtures each comprise 0.5 µg/ml test substance as well as 0.2-0.5 mg/ml microsomal protein. In addition, 0.05 M phosphate buffer (pH=7.4), 1 mM EDTA, 5 mM glucose 6-phosphate and 1.5 U/ml glucose-6-phosphate dehydroxygenase from *Leuconostoc Mesenteroides* are added. The microsomal incubation is started by adding NADP$^+$ (final concentration: 1 mM).

In each case 1 million cells/ml are used to determine the metabolic stability of the test substances in freshly isolated and cultivated rat, dog and human hepatocytes. In a manner equivalent to the microsomal assay, in each case 0.5 µg/ml test substance are added to the hepatocytes.

125 µl are removed from the respective incubation mixture after 2, 5, 10, 20, 30, 45 and 60 min, or after 2, 10, 20, 30, 50, 70 and 90 min for more stable compounds, and ACN is added in order to stop the enzymatic reactions. After centrifugation, the samples are analyzed by LC-MS/MS (API 2000 or 3000, Applied Biosystems). "CL$_{blood}$ well-stirred" and "F$_{max}$ well-stirred" values are calculated from the respective half-lives of the compounds in the microsomal incubations. The substrate degradation can be described by the following formulae (Houston J B, Utility of in-vitro drug-metabolism data in predicting in-vivo metabolic-clearance, Bioch. Pharm. 47 (9)

1469-1479 (1994); Obach R S; Baxter J G; Liston T E; Silber B M; Jones B C; MacIntyre F; Rance D J; Wastall P, The prediction of human pharmacokinetic parameters from preclinical and in vitro metabolism data, J. Pharmacol. Exp. Ther. 283 (1) 46-58 (1997)):

$CL'_{intrinsic}$[ml/(min·kg)]=(0.693/in vitro $t_{1/2}$ [min])·(liver weight [g liver/kg body weight])·(microsomal protein [mg]/liver weight [g])/(microsomal protein [mg]/incubation volume [ml]).

The blood clearance "$CL_{blood}$" is described by the "well-stirred" model, ignoring protein bindings (Pang K S; Rowland M, Hepatic clearance of drugs. I. Theoretical considerations of a "well-stirred" model and a "parallel tube" model. Influence of hepatic blood flow, plasma and blood cell binding, and the hepatocellular enzymatic activity on hepatic drug clearance, *J Pharmacokinet Biopharm* 5 (6): 625-53 (1977)):

$CL_{blood}$ well-stirred[l/(h·kg)]=($Q_H$[l/(h·kg)]·$CL'_{intrinsic}$[l/(h·kg)])/($Q_H$[l/(h·kg)]+ $CL'_{intrinsic}$[l/(h·kg)]).

For rats, the specific liver weight is 32 g/kg of body weight and the hepatic blood flow is 4.2 l/(h·kg). The specific microsomal protein content of the rat liver was estimated at 40 mg/g of liver. The specific extrapolation factors for further species are shown in the following table and are based in part on literature data and in part on our own determinations. For hepatocytes a cell count of 110 million/g of liver is used for the calculation for all species.

|  | Mouse m | Mouse f | Rat m | Dog m/f | Human m/f |
|---|---|---|---|---|---|
| Microsomal protein/g of liver [mg] | 40 | 40 | 40 | 40 | 40 |
| Liver [g]/kg of body weight | 50 | 43 | 32 | 39 | 21 |
| Liver blood flow [l/(h · kg)] | 5.4 | 5.4 | 4.2 | 2.1 | 1.32 |

C) Exemplary Embodiments of Pharmaceutical Compositions

The compounds of the invention can be converted into pharmaceutical preparations in the following ways:
Tablet:
Composition:
100 mg of the compound of Example 1, 50 mg of lactose (monohydrate), 50 mg of corn starch (native), 10 mg of polyvinylpyrrolidone (PVP 25) (from BASF, Ludwigshafen, Germany) and 2 mg of magnesium stearate.
Tablet weight 212 mg, diameter 8 mm, radius of curvature 12 mm
Production:
The mixture of compound of the invention, lactose and starch is granulated with a 5% solution (m/m) of the PVP in water. The granules are mixed with the magnesium stearate for 5 minutes after drying. This mixture is compressed with a conventional tablet press (see above for format of the tablet). A guideline compressive force for the compression is 15 kN.
Solution which can be Administered Orally:
Composition:
500 mg of the compound of Example 1, 2.5 g of polysorbate and 97 g of polyethylene glycol 400.20 g of oral solution correspond to a single dose of 100 mg of the compound of the invention.

Production:
The compound of the invention is suspended in the mixture of polyethylene glycol and polysorbate with stirring. The stirring process is continued until the compound of the invention has completely dissolved.
i.v. Solution:
The compound of the invention is dissolved in a concentration below the saturation solubility in a physiologically tolerated solvent (e.g., isotonic saline solution, 5% glucose solution, 30% PEG 400 solution). The solution is sterilized by filtration and used to fill sterile and pyrogen-free injection containers.

What is claimed is:
1. A compound of formula

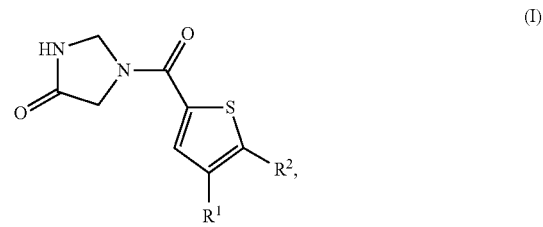

(I)

in which
$R^1$ represents phenyl,
whereby phenyl is substituted with 1 to 3 substituents, whereby the substituents are selected independently of one another from the group consisting of halogen, hydroxy, cyano, nitro, trifluoromethyl, trifluoromethoxy, trifluoromethylthio, ($C_1$-$C_4$)-alkyl and ($C_1$-$C_4$)-alkoxy,
wherein
($C_1$-$C_4$)-alkyl and ($C_1$-$C_4$)-alkoxy in turn may be substituted one to three times identically or differently with radicals selected from the group consisting of halogen, cyano, hydroxy, ($C_1$-$C_4$)-alkoxy, amino, mono-($C_1$-$C_4$)-alkylamino, di-($C_1$-$C_4$)-alkylamino, ($C_3$-$C_7$)-cycloalkyl and 4-to 7-membered heterocyclyl,
whereby the last-mentioned cycloalkyl and heterocyclyl radicals in turn may be substituted up to three times identically or differently with substituents selected from the group consisting of halogen, cyano, ($C_1$-$C_4$)-alkyl, trifluoromethyl, hydroxy, ($C_1$-$C_4$)-alkoxy, trifluoromethoxy, oxo, amino, mono-($C_1$-$C_4$)-alkylamino and di-($C_1$-$C_4$)-alkylamino, and
$R^2$ represents phenyl,
whereby phenyl is substituted with 1 to 3 substituents, whereby the substituents are selected independently of one another from the group consisting of halogen, hydroxy, cyano, nitro, trifluoromethyl, trifluoromethoxy, trifluoromethylthio, ($C_1$-$C_4$)-alkyl and ($C_1$-$C_4$)-alkoxy,
wherein
($C_1$-$C_4$)-alkyl and ($C_1$-$C_4$)-alkoxy in turn may be substituted one to three times identically or differently with radicals selected from the group consisting of halogen, cyano, hydroxy, ($C_1$-$C_4$)-alkoxy, amino, mono-($C_1$-$C_4$)-alkylamino, di-($C_1$-$C_4$)-alkylamino, ($C_3$-$C_7$)-cycloalkyl and 4-to 7-membered heterocyclyl,
whereby the last-mentioned cycloalkyl and heterocyclyl radicals in turn may be substituted up to three times identically or differently with substituents selected from the group consisting of halogen, cyano, ($C_1$-$C_4$)-alkyl, trifluoromethyl, hydroxy, (C₁-C₄)-alkoxy, trifluoromethoxy, oxo, amino, mono-(C₁-C₄)-alkylamino and di-(C₁-C₄)-alkylamino,
or one of the salts thereof.

2. The compound of claim 1, whereby
R¹ represents phenyl,
whereby phenyl is substituted with 1 to 2 substituents, whereby the substituents are selected independently of one another from the group consisting of halogen, hydroxy, cyano, nitro, trifluoromethyl, trifluoromethoxy, trifluoromethylthio, (C₁-C₄)-alkyl and (C₁-C₄)-alkoxy, and
R² represents phenyl,
whereby phenyl is substituted with 1 to 2 substituents, whereby the substituents are selected independently of one another from the group consisting of halogen, hydroxy, cyano, nitro, trifluoromethyl, trifluoromethoxy, trifluoromethylthio, (C₁-C₄)-alkyl and (C₁-C₄)-alkoxy,
wherein
(C₁-C₄)-alkoxy in turn may be substituted one or three times identically or differently with radicals selected from the group consisting of halogen, cyano, hydroxy, (C₁-C₄)-alkoxy, amino, mono-(C₁-C₄)-alkylamino, di-(C₁-C₄)-alkylamino, (C₃-C₇)-cycloalkyl and 4- to 7-membered heterocyclyl,
whereby the last-mentioned cycloalkyl and heterocyclyl radicals in turn may each be substituted up to three times identically or differently with halogen, cyano, (C₁-C₄)-alkyl, trifluoromethyl, hydroxy, (C₁-C₄)-alkoxy, trifluoromethoxy, oxo, amino, mono-(C₁-C₄)-alkylamino, or di-(C₁-C₄)-alkylamino,
or one of the salts thereof.

3. The compound of claim 1, whereby
R¹ represents phenyl,
whereby phenyl is substituted with 1 to 2 substituents, whereby the substituents are selected independently of one another from the group consisting of halogen, cyano, trifluoromethyl, methyl and methoxy,
R² represents phenyl,
whereby phenyl is substituted with 1 to 2 substituents, whereby the substituents are selected independently of one another from the group consisting of halogen, cyano, trifluoromethyl, trifluoromethoxy, methyl and (C₁-C₃)-alkoxy,
or one of the salts thereof.

4. The compound of claim 1, corresponding to formula

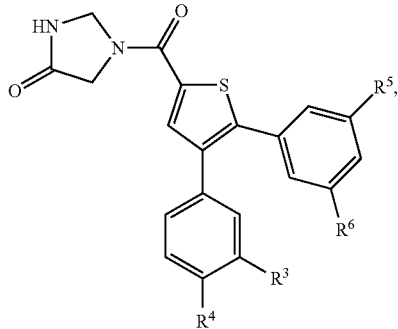

(Ia)

in which
R³ represents halogen or cyano,
R⁴ represents hydrogen or halogen,
R⁵ represents halogen, cyano or trifluoromethyl, and
R⁶ represents hydrogen or halogen,
or one of the salts thereof.

5. The compound of claim 4, whereby
R³ represents fluorine, chlorine or cyano,
R⁴ represents hydrogen, chlorine or fluorine,
R⁵ represents fluorine, chlorine or cyano, and
R⁶ represents hydrogen, chlorine or fluorine,
or one of the salts thereof.

6. The compound of claim 4, whereby
R³ represents chlorine or cyano,
R⁴ represents hydrogen or fluorine,
R⁵ represents chlorine or cyano, and
R⁶ represents hydrogen or fluorine,
or one of the salts thereof.

7. A method for preparing a compound of formula (I) of claim 1, comprising reacting a compound of formula

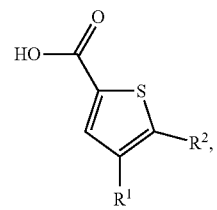

(II)

in which
R¹ and R² have the meaning given in claim 1,
with imidazolidin-4-one or with a salt of imidazolidin-4-one.

8. A method for preparing a compound of formula (I) of claim 1, comprising reacting a compound of formula

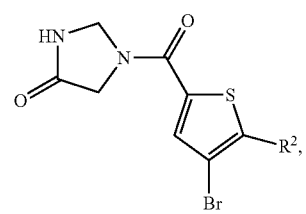

(VIII)

in which
R² has the meaning given in claim 1,
under Suzuki coupling conditions with a compound of formula

R¹-Q        (V), in which
R¹ has the meaning given in claim 1 and
Q represents —B(OH)₂, a boronic acid ester, boronic acid pinacol ester, or —BF₃⁻K⁺.

9. A method for preparing a compound of formula (I) of claim 1, comprising reacting a compound of formula

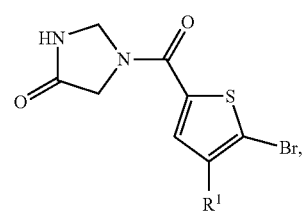

(X)

in which $R^1$ has the meaning given in claim 1, under Suzuki coupling conditions with a compound of formula $$R^2\text{-Q} \qquad (VII),$$

in which $R^2$ has the meaning given in claim 1 and

Q represents —B(OH)$_2$, a boronic acid ester, boronic acid pinacol ester, or —BF$_3^-$K$^+$.

10. A method for the manufacture of a medicament for the treatment of retroviral diseases comprising mixing a compound of claim 1 with an inert, non-toxic, pharmaceutically acceptable excipient.

11. A medicament comprising a therapeutically effective amount of at least one compound of claim 1 in combination with at least one inert, non-toxic, pharmaceutically acceptable excipient.

12. A method for controlling HIV-1 infections in humans and animals by administering an antivirally effective amount of at least one compound of claim 1 or a medicament of claim 11 to a human or animal in need thereof.

* * * * *